United States Patent [19]

Walters et al.

[11] 4,055,783
[45] Oct. 25, 1977

[54] SPARK SOURCE WITH REGULATION OF SPARK MAGNITUDE BY CONTROL OF SPARK TIMING

[75] Inventors: John P. Walters; David M. Coleman, both of Madison, Wis.

[73] Assignee: Wisconsin Alumni Research Foundation, Madison, Wis.

[21] Appl. No.: 662,891

[22] Filed: Mar. 1, 1976

[51] Int. Cl.² .......................... G01J 3/30; H05B 7/20
[52] U.S. Cl. .............................. 315/241 R; 315/208;
315/240; 315/243; 315/244; 356/86
[58] Field of Search .......... 315/207, 208, 240, 241 R, 315/243, 244; 356/86

[56] References Cited

U.S. PATENT DOCUMENTS

| | | | |
|---|---|---|---|
| 3,749,975 | 7/1973 | Walters | 315/241 R |
| 3,906,291 | 9/1975 | Schayes et al. | 356/86 X |
| 3,973,167 | 8/1976 | Walters et al. | 315/240 X |

*Primary Examiner*—Eugene R. LaRoche
*Attorney, Agent, or Firm*—Burmeister, York, Palmatier, Hamby & Jones

[57] ABSTRACT

The disclosed spark source is adapted to generate electrical sparks to produce light for spectroscopic analysis of materials placed on the spark gap electrodes or introduced into the sparks. The disclosed spark source comprises a high voltage transformer having a secondary winding for supplying alternating current at a high voltage, a storage capacitor, a charging circuit including a rectifier connected between the secondary winding and the capacitor for charging the capacitor, spark gap electrodes having a spark gap therebetween, a discharge circuit including an electronic switching device connected between the capacitor and the spark gap electrodes for discharging the capacitor across the spark gap and control means for supplying a sequence of variably spaced triggering pulses to the input means of the electronic switching device for producing a sequence of spark cycles in which the capacitor is charged to substantially the same voltage for all of the spark cycles. During the intervals between sparks, the capacitor is recharged by the transformer and the rectifier. The timing of the sparks is varied, with reference to the phase angle of the alternating current, so that the capacitor is charged to the same voltage during each of the intervals between sparks. The timing of the sparks is computed to accommodate the variation in the instantaneous voltage developed by the transformer during such intervals. By varying the timing of the sparks, it is possible to vary the voltage to which the capacitor is charged, over a wide range. The electronic switching device may comprise a thyratron in parallel with a shunting diode, to carry the oppositely polarized half-cycles of the oscillatory capacitor discharge current. An inductance element may be connected in series with the thyratron to improve the commutation between the thyratron and the shunting diode. It is also advantageous to insert an inductance element in series with the shunting diode to bring about a further improvement in such commutation.

22 Claims, 14 Drawing Figures

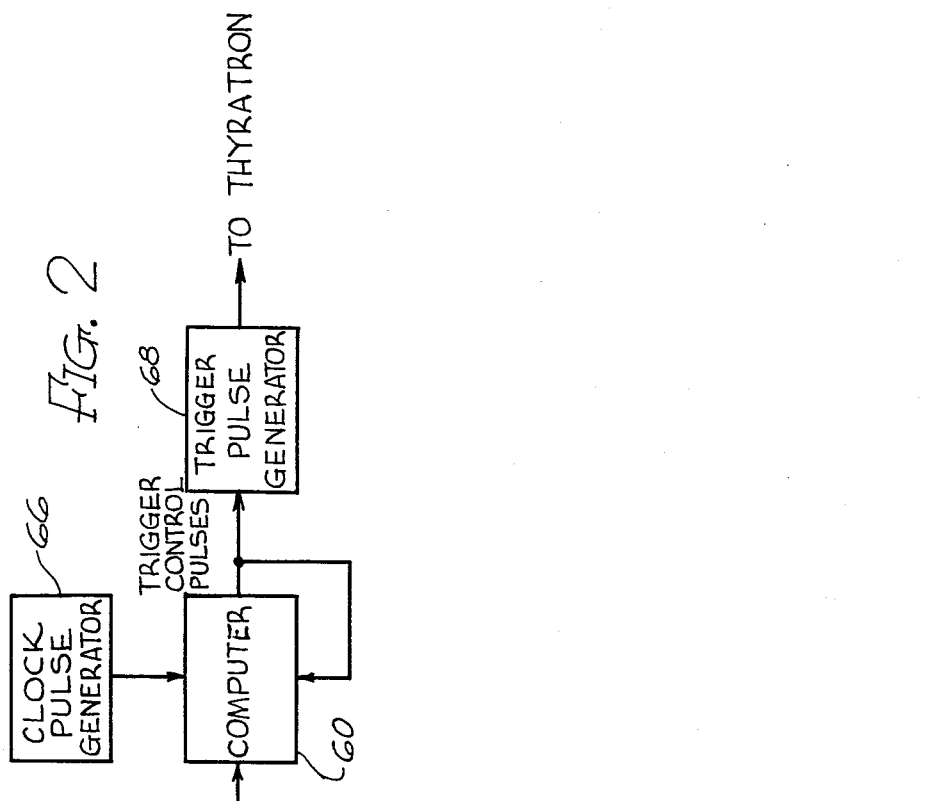
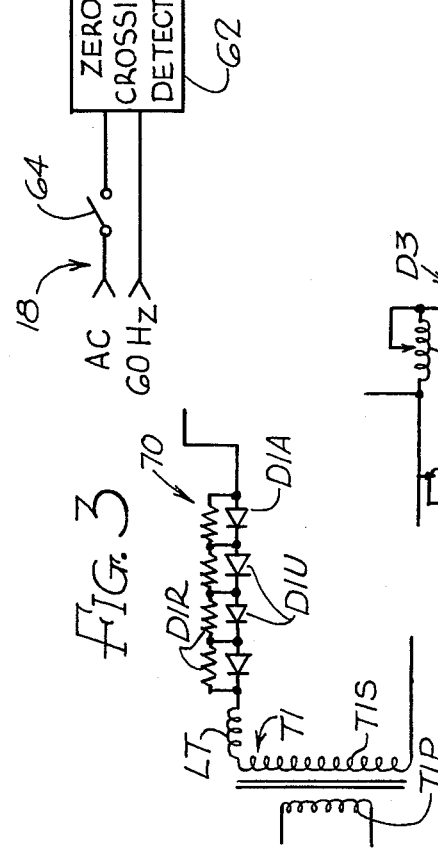
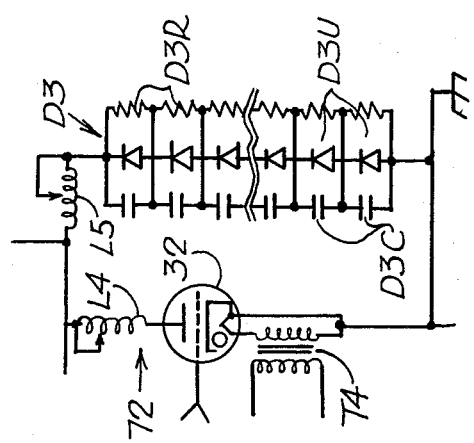

FIG. 8
C = 0.003 μF
R = 20 K
E = 10000 V
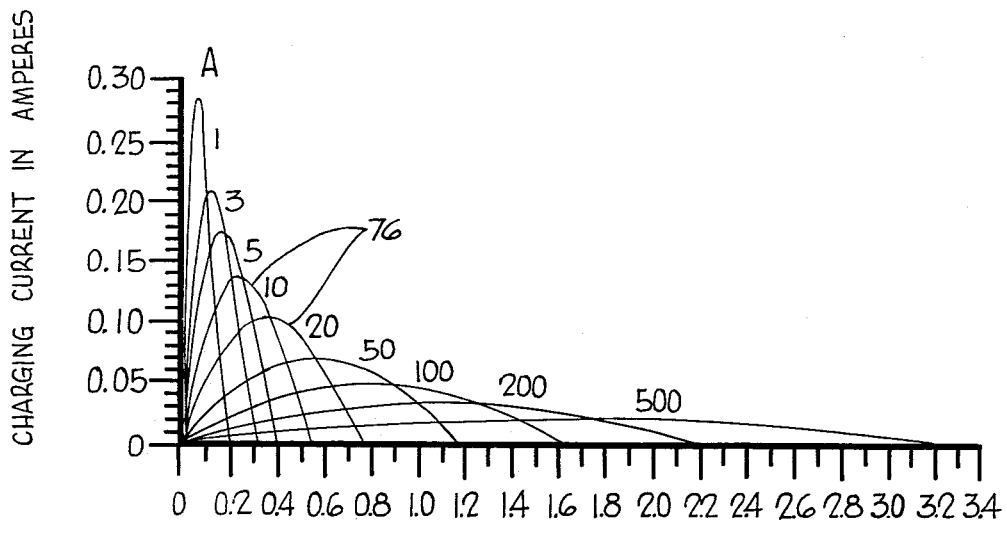
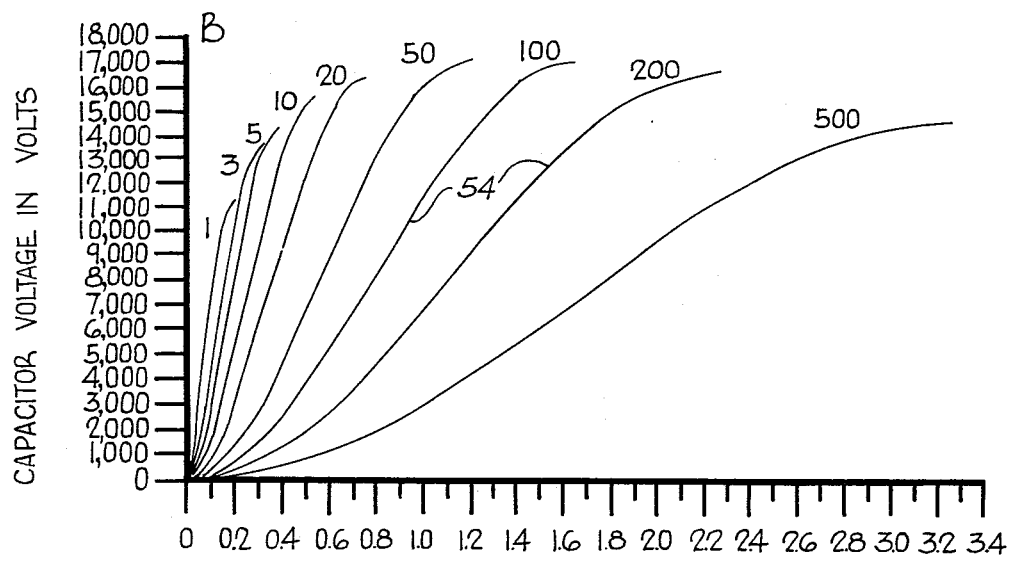
TIME FROM LINE VOLTAGE MAXIMUM (ZERO PHASE REFERENCE) IN MILLISECONDS FIG. 9
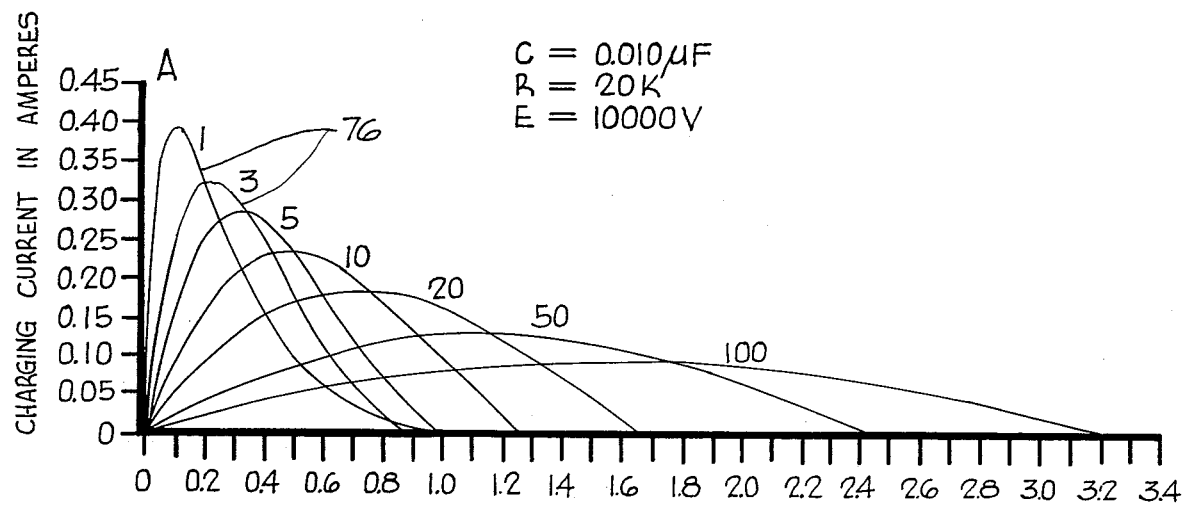
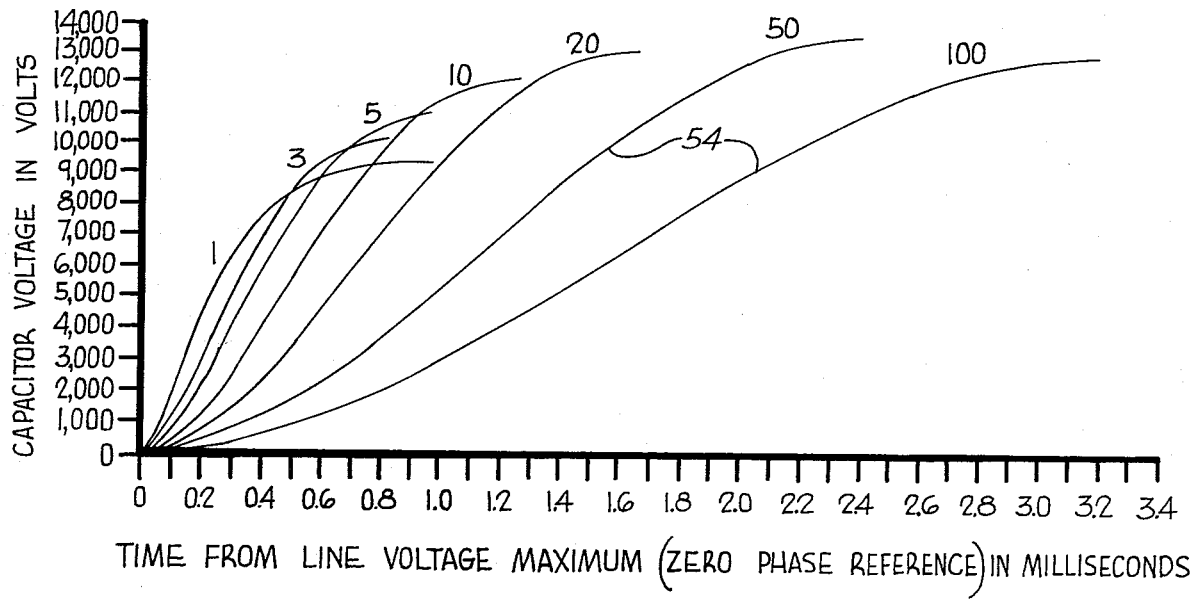
TIME FROM LINE VOLTAGE MAXIMUM (ZERO PHASE REFERENCE) IN MILLISECONDS VERTICAL = 100 AMPS/CM
HORIZONTAL = 5 $\mu$SEC/CM
$C_1$ = 0.0625 $\mu$F
$L_1$ = 85 $\mu$H
$L_2$ = 8.8 $\mu$H VERTICAL = 100 AMPS/CM
HORIZONTAL = 5 $\mu$SEC/CM
$C_1$ = 0.0625 $\mu$F
$L_1$ = 150 $\mu$H
$L_2$ = 8.8 $\mu$H

SPARK SOURCE WITH REGULATION OF SPARK MAGNITUDE BY CONTROL OF SPARK TIMING

The Government has rights in this invention pursuant to Grant No. MPS 72-04971 and IPA No. 0001 awarded by the National Science Foundation.

This invention relates to spark sources for producing electrical sparks for any desired purpose, particularly to produce light for emission spectroscopy.

In electrical spark emission spectroscopy, electrical sparks are produced across a spark gap between two spark electrodes. A material to be analyzed is introduced into the sparks, so that the material is caused to emit light having a spectrum which is characteristic of that material. The light is then analyzed by the usual procedures of emission spectroscopy.

The material may be in the gaseous, liquid or solid state when introduced into the sparks. When the material is a solid, it is generally placed on or made the material of one or both of the electrodes. The material is then eroded and vaporized by the sparks so as to produce its characteristic spectrum.

One principal object of the present invention is to provide a spark source capable of producing a train or series of repetitive sparks which are regulated in magnitude or energy in a new and improved manner, so that the magnitude of the sparks can be kept constant or otherwise regulated.

It has been found that it is desirable to keep the magnitude of the sparks constant in order to carry out spectroscopic analyses which are repeatable and quantitatively accurate to a high degree. If the magnitude of the sparks is kept constant, there will be a definite quantitative relationship between the concentration of any particular constituent of the material being analyzed and the amount of light in the spectral lines produced by such constituent. With the control over the magnitude of the sparks afforded by the present invention, spectroscopic analyses can be carried out to determine not only the identity of the various constituents of the material being analyzed, but also the concentration of each constituent with an improved degree of accuracy.

The present invention in various aspects is an improvement over the invention disclosed and claimed in the copending application of John P. Walters and John A. Bernier, Ser. No. 568,577, filed Apr. 16, 1975 and entitled, "Spark Sources With Electronic Switching Tubes", now U.S. Pat. No. 3,973,167, issued Aug. 3, 1976. The present invention is applicable to spark sources of the general construction disclosed in such copending application. In such a spark source, the sparks are produced across a spark gap between two electrodes, by discharging a capacitor across the spark gap. The production of each spark is controlled by the triggering of a thyratron or some other electronic switching device, connected into a discharge circuit between the capacitor and the spark gap. The provision of the electronic switching device makes it possible to control the timing of each spark with a high degree of precision. After each spark, the capacitor is recharged to a high voltage by a charging circuit comprising a high voltage transformer and a rectifier.

In accordance with the present invention, it has been found that the magnitude of the individual sparks in a train or series of sparks can be regulated and controlled by varying the timing of the individual sparks in the train. The variation in the timing of each spark affects the voltage to which the capacitor is charged for the next spark. By varying the timing of the individual sparks, it is possible to charge the capacitor to the same voltage for all of the sparks in the series or train. When this is done, all of the sparks will be the same in magnitude or energy. Moreover, the waveform of the spark discharge current will be the same for all of the sparks. Accordingly, the spectral characteristics of the light emitted by all the sparks will be the same, both as to magnitude and detailed structure.

In some cases, it may be desired to vary the magnitude of the individual sparks in a predetermined manner. This can also be accomplished by varying the timing of the sparks.

It has been found that if the timing of the sparks is not varied, so that the repetition rate of the sparks is kept constant, the magnitude of the sparks will not be constant, but will vary throughout the cycle of the alternating current which is employed to energize the high voltage transformer.

In order to keep the magnitude of the sparks constant, the timing of the sparks may be varied under the control of a computer, which may be programmed to vary the timing of each spark in accordance with the instantaneous timing of the rectified alternating current supplied by the transformer secondary and the rectifier.

As disclosed in the previously mentioned Walters and Bernier application, the thyratron employed as the electronic switching device is preferably shunted by a reverse connected diode for carrying the reversely polarized half-cycles of the oscillatory spark discharge current in the discharge circuit. To improve the commutation between the thyratron and the shunting diode, inductance may be inserted in series with the thyratron. Such inductance may be sufficiently great in magnitude to substain the thyratron current so as to prevent deionization of the thyratron during the half-cycles when the shunting diode is conductive. This construction minimizes or obviates the production of voltage spikes and other transients across the thyratron, and also minimizes or obviates irregularities in the total time span of the spark discharges.

Further objects, advantages and features of the present invention will appear from the following description, taken with the accompanying drawings, in which:

FIG. 2 is a schematic diagram showing the timing control for the spark source of FIG. 1.

FIG. 3 is a fragmentary schematic circuit diagram showing a modified construction utilizing a half-wave rectifier rather than a full-wave rectifier, as in FIG. 1.

FIG. 4 is a schematic circuit diagram showing a modified construction in which inductance is introduced in series with the thyratron of FIG. 1.

FIG. 8 is a series of waveform diagrams showing the capacitor charging current and voltage for different values of inductance in the charging circuit.

FIG. 9 is a series of waveform diagrams similar to those of FIG. 8, but for a different value of capacitance.

Figure 1:
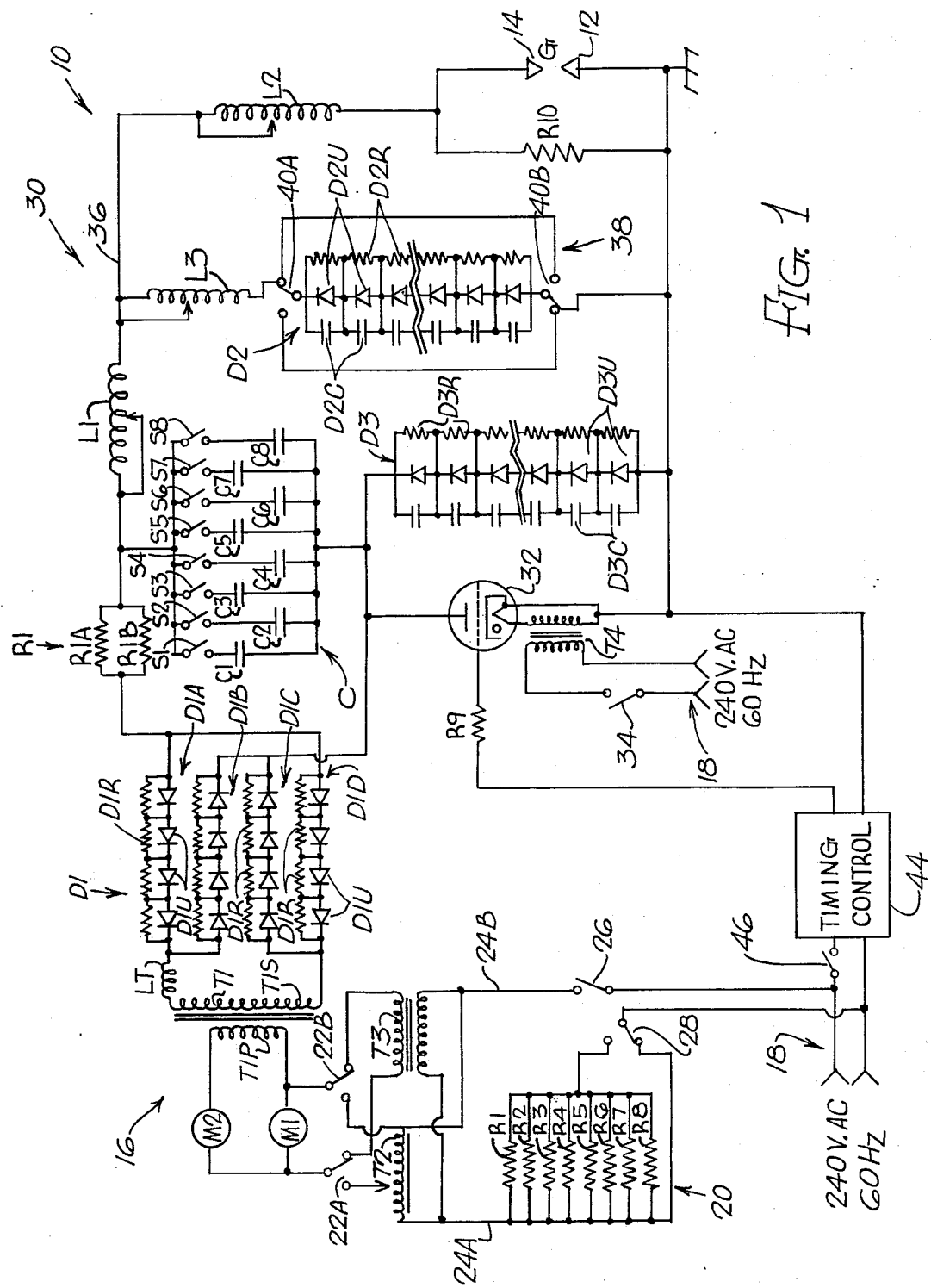
FIG. 1 is a schematic circuit diagram of a spark source to be described as an illustrative embodiment of the present invention.

FIG. 1 illustrates a spark source 10 of the general construction disclosed and claimed in the previously mentioned Walters and Bernier application. In the spark source 10, the electrical sparks are produced across a spark gap G between a grounded electrode 12 and an ungrounded electrode 14. The sparks are produced by discharging a high voltage capacitor C across the spark gap G. While the capacitor C may comprise a single capacitor unit, if desired, the illustrated construction employs a plurality of capacitor units C1, C2, C3, C4, C5, C6, C7 and C8 adapted to be connected in parallel on a selective basis by corresponding switches S1–S8. By operating the switches, any or all of the capacitor units C1–C8 can be connected in parallel, so that the total capacitance of the capacitor C can be varied.

The capacitor C is adapted to be charged by a charging circuit 16 comprising a high voltage transformer T1, a diode rectifier D1 and a series resistor R1. The transformer T1 comprises a low voltage primary winding T1P and a high voltage secondary winding T1S.

The diode rectifier D1 may be of the full-wave type or the half-wave type, and may comprise one or more diode units. As shown, the diode rectifier D1 is of the full-wave type, utilizing four diode stacks D1A, D1B, D1C, and D1D in a bridge circuit. Each diode stack comprises a plurality of diode units D1U connected in series. In each stack, the diode units D1U are shunted by high value resistors D1R which provide a voltage divider for equalizing the voltage distribution along the diode stack.

While the resistor R1 may comprise a single resistor unit, the illustrated construction utilizes two resistor units R1A and R1B connected in parallel, to double the wattage rating.

In the charging circuit 16, an inductance LT is shown in series with the secondary winding T1S of the high voltage transformer T1. This inductance LT represents the effective inductance in series with the charging circuit, such effective inductance being produced by the leakage inductance of the transformer T1 and any additional or lumped inductance inserted into the charging circuit. Typically, no additional lumped inductance is provided, so that the inductance LT represents the effective inductance produced by the transformer T1. Such effective inductance is generally the primary inductance multiplied by the square of the turns ratio of the transformer T1.

The primary winding T1P of the high voltage transformer T1 is adapted to be energized from a pair of alternating current power lines 18 which may supply alternating current at 240 Volts and 60 Hz or any other suitable voltage and frequency. While the primary winding T1P could be connected directly to the power lines 18, the illustrated construction provides a primary circuit 20 which makes it possible to control and vary the voltage applied to the primary T1P. As shown, a voltmeter M1 is connected across the primary winding T1P to measure the primary voltage, while an ammeter M2 is connected in series with the primary winding to measure the primary current. The opposite sides of the primary winding T1P are connected to a pair of two-position selector switches 22A and B, whereby the primary winding can be connected to either the output terminals of a variable autotransformer T2 or the secondary winding of a transformer T3. The input connections of the variable autotransformer T2 and the primary winding of the transformer T3 are connected in parallel to leads 24A and B. It will be seen that a switch 26 is connected between the lead 24B and one of the power lines 18. The other power line is connected to a two-position selector switch 28. In one position, the switch 28 establishes a direct connection between the power line and the lead 24A. In the other position, the switch 28 establishes a connection through a bank of resistors R1–R8, connected in parallel to provide the desired wattage rating. It will be understood that the insertion of the resistors R1–R8 reduces the voltage supplied to the primary winding T1P of the high voltage transformer T1.

The spark source 10 of FIG. 1 includes a discharge circuit 30 which includes the capacitor C and the spark gap G, for discharing the capacitor across the spark gap. The discharge circuit 30 includes an electronic switching device, illustrated as a thyratron gaseous discharge tube 32. In the illustrated circuit, the thyratron 32 is polarized with its anode connected to one side of the capacitor C, and with its cathode connected to ground, and thus to the grounded electrode 12 of the spark gap G. The thyratron 32 could be connected elsewhere in the discharge circuit 30, with the polarization of the thyratron reversed, but it is advantageous to connect the thyratron 32 so that its cathode is grounded. As shown, the heater of the thyratron 32 is energized from the secondary of a transformer T4, having its primary connected to the alternating current power lines 18 through a switch 34. The control electrode of the thyratron 32 is adapted to receive triggering pulses to cause the thyratron to become conductive, as will be described in greater detail presently.

In the illustrated spark source 10, the discharge circuit 30 includes inductors or inductance elements L1 and L2, connected in series between the high voltage side of the capacitor C and the ungrounded electrode 14 of the spark gap G. The inductance elements L1 and L2 are preferably variable or adjustable, as shown, but may also be fixed. A junction lead 36 is provided between the inductance elements L1 and L2.

As described in the previously mentioned Walters and Bernier application, a shunting diode D2 is preferably connected in a shunting path 38 which extends between the junction lead 36 and ground. Thus, the shunting path 38 is arranged to shunt the series combination of the spark gap G and the inductance element L2. The shunting path 38 preferably includes a third inductance element or inductor L3, connected in series with the shunting diode D2. The inductance element L3 is preferably variable or adjustable, as shown, but may also be fixed.

The illustrated shunting path includes a pair of two-position selector switches 40A and B for reversing the polarity of the shunting diode D2. When the switches 40A and B are in the positions shown in FIG. 1, the diode D2 is polarized to conduct current between ground and the junction lead 36. When the switches 40A and B are in their other positions, the diode D2 is polarized to conduct current between the junction lead 36 and ground. The shunting diode D2 could possibly include only a single diode unit having a sufficiently high inverse voltage rating, but it is preferred to employ a diode stack having a plurality of diode units D2U in series. The diode units D2U are preferably shunted by corresponding high value resistors D2R to provide a voltage divider for evenly distributing the inverse voltage along the diode stack D2. Shunting capacitors D2C are also provided across the respective diode units D2U to provide a similar voltage dividing action.

Figure 10:
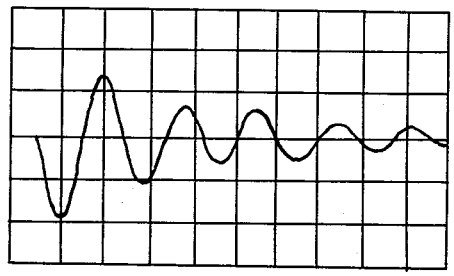
FIG. 10 is a wave form diagram representing the oscillatory discharge current in the capacitor discharge circuit.

Due to the presence of capacitance, conductance and resistance in the discharge circuit 30, the capacitor discharge current is of a damped oscillatory character. FIG. 10 shows a damped oscillatory waveform which is a typical representation of the capacitor discharge current. It will be understood that the thyratron 32 acts as a rectifier and thus conducts the oscillatory discharge current in one direction only, during the half-cycles of the discharge current which are polarized to cause current to flow between the anode and the cathode of the thyratron 32. To carry the discharge current during the reverse half-cycles, the thyratron 32 is preferably shunted by a shunting diode D3, polarized to conduct current between ground and the capacitor C. The diode D3 could possibly comprise only a single diode unit having a sufficiently high inverse voltage rating, but it is preferred to employ the illustrated diode stack, comprising a plurality of diode units D3U connected in series. Shunting resistors D3R of high value are preferably connected across the respective diode units D3U to provide a voltage divider which will equalize the distribution of the inverse voltage along the diode stack D3. Shunting capacitors D3C of small value are also preferably connected across the diode units D3U to provide a similar voltage dividing action.

As shown in FIG. 1, a protective resistor R9 is preferably connected in series with the control electrode of the thyratron 32. A shunting resistor R10 is preferably connected between the spark gap electrodes 12 and 14 to discharge the capacitor C completely when the spark source 10 is shut down, and to prevent premature ignition of the spark across the spark gap, before the thyratron 32 is triggered into a conductive state. Such premature ignition of the spark may be produced due to distributed capacitance between the anode of the thyratron 32 and ground, as explained in the previously mentioned Walters and Bernier application.

As previously indicated, the thyratron 32 is triggered into conduction by pulses or other suitable triggering signals supplied to the control electrode of the thyratron 32 through the resistor R9. Thus, the thyratron 32 acts as an electronic switching device. When the thyratron 32 becomes conductive, the capacitor C is discharged through the discharge circuit 30. The discharge of the capacitor C produces a spark across the spark gap G. Due to the presence of capacitance, inductance and resistance in the discharge circuit 30, the discharge current is oscillatory and has a damped oscillatory waveform, as represented in a general way in FIG. 10. The thyratron 32 conducts the capacitor discharge current during the half-cycles of one polarity, while the shunting diode D3 conducts the discharge current during the half-cycles of the opposite polarity.

During the oscillatory discharge of the capacitor C, the waveform of the spark current across the spark gap G is modified by the presence of the shunting diode D2, as explained in the previously mentioned Walters and Bernier application, and also in the Walters U.S. Pat. No. 3,749,975, issued July 31, 1973. The shunting diode D2 is conductive in one direction only. The effect of the shunting diode D2 upon the spark current depends upon the polarity of the diode D2. As shown in FIG. 1, the shunting diode D2 is polarized so as to be conductive during the first half-cycle of the capacitor discharge current. If the inductance of L3 is very low, approaching zero, and if the impedance of the shunting diode D2 is sufficiently low, the spark gap G may not even be broken down into conduction during the first half-cycle of the capacitor discharge current. If the impedance of the shunting diode D2 is higher, or if L3 has a sufficient inductance, the spark gap G will be broken down into conduction during the first half-cycle. It is generally preferred to keep the impedance of D2 and the inductance of L3 to a minimum, so that little or no current will flow across the spark gap G during the first half-cycle of the capacitor discharge current.

During the second half-cycle of the capacitor discharge current, the shunting diode D2 becomes non-conductive, due to the reversal of the current, so that the spark gap G breaks down and becomes conductive. The spark current flows through the inductance L2, so that energy is stored in the magnetic field which is produced by the current in the inductance L2.

During the third half-cycle, the shunting diode D2 again becomes conductive, but the conduction across the spark gap G is also maintained, with the direction of the spark current unchanged, by the inductance L2. The energy stored in the magnetic field of the inductance L2 is released as the magnetic field gradually collapses, with the result that a voltage is induced in L2 so as to sustain the spark current across the spark gap G. It is generally preferred to make the inductance of L2 sufficiently high to sustain the spark current across the spark gap G for the remainder of the damped oscillatory discharge current of the capacitor C. Thus, the spark current has a unidirectional pulsating waveform during the second and subsequent half-cycles of the capacitor discharge current.

Figure 11:
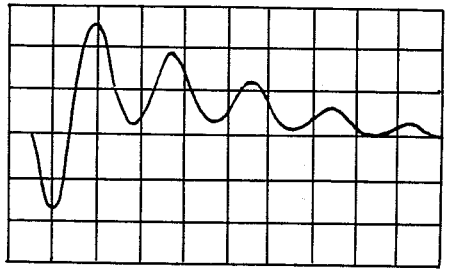
FIG. 11 is a waveform diagram representing the modified discharge current across the spark gap.
Figure 12:
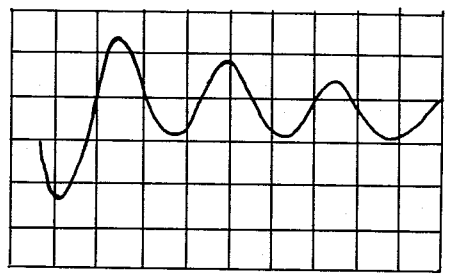
FIG. 12 is a waveform diagram similar to FIG. 11, but for a different value of capacitance.

The waveform of the spark current is represented by FIGS. 11 and 12, which show that the spark current is unidirectional and pulsating during the second and subsequent half-cycles. In the situation represented by FIGS. 11 and 12, there is a reverse spark current during the first half-cycle, but this reverse current can be eliminated by making the impedance of the shunting diode D2 and the inductance of L3 sufficiently low.

The waveforms of FIGS. 11 and 12 are similar, but specifically different, because the waveform of FIG. 12 was obtained with a higher value of the inductance L1 than was employed to produce the waveform of FIG. 11. Thus, FIG. 12 represents a condition in which L1 had a value of 150 microhenrys, while FIG. 11 represents a condition in which L1 had a value of 85 microhenrys.

As explained in the previously mentioned Walters and Bernier application, the unidirectional spark current during the second and subsequent half-cycles is advantageous, because the material to be analyzed is eroded and vaporized almost entirely from the grounded spark gap electrode 12, which functions as the cathode during the second and subsequent half-cycles.

The frequency of the oscillatory capacitor discharge current is inversely related to the values of the capacitance and the inductance in the capacitor discharge circuit. Specifically, the oscillatory frequency is inversely proportional to the square root of the capacitance and inversely proportional to the square root of the inductance. Thus, as will be evident from a comparison of FIGS. 11 and 12, the oscillatory frequency is greater for the condition represented in FIG. 11, in which the inductance of L1 is less than in the condition represented by FIG. 12. To restate the same proposition in another way, the period of the oscillatory current is less for the condition of FIG. 11, in which the inductance is less.

As will be evident from FIG. 10, the oscillatory capacitor discharge current is damped, because the energy initially stored in the capacitor C is dissipated by the effective resistance of the spark across the spark gap G, and also by the resistances of the inductances and conductors in the discharge circuit. Thus, the oscillatory capacitor discharge current dies out after a brief period of time, comprising a number of cycles of the oscillatory capacitor discharge current. Thus, the spark gap G becomes nonconductive. The thyratron 32 also becomes nonconductive because the triggering pulse supplied to its control electrode is terminated.

As shown in FIG. 1, the triggering pulses are supplied to the control electrode of the thyratron 32 by a timing control device or means 44, which supplies the pulses between the control electrode and the grounded cathode of the thyratron. As will be explained in greater detail presently, the timing of the pulses supplied by the timing control 44 is related to the phase angle of the alternating current supplied by the alternating current power lines 18. Thus, in the construction of FIG. 1, the alternating current power lines 18 are connected to the timing control 44 through a switch 46.

When the capacitor discharge current dies out and the spark gap G becomes nonconductive, the capacitor C is recharged by the charging circuit 16, comprising the secondary winding T1S of the high voltage transformer T1, the diode rectifier D1 and the series resistor R1. The waveform of the charging current and the rapidity with which the capacitor C is recharged are determined by the voltage developed in the secondary winding T1S, the effective charging inductance LT, and the charging circuit resistance afforded primarily by R1, but also by the diode rectifier D1 and the secondary winding T1S. For simplicity of discussion, R1 may be regarded as incorporating not only its own resistance, but the resistances contributed by the diode rectifier D1 and the transformer secondary T1S.

It has been found that the timing of the sparks has a surprisingly great effect upon the magnitude of the voltage to which the storage capacitor C is charged between sparks. The timing of the sparks can be varied by changing the timing of the triggering pulses supplied to the control electrode of the thyratron 32 by the timing control means 44.

Figure 5:
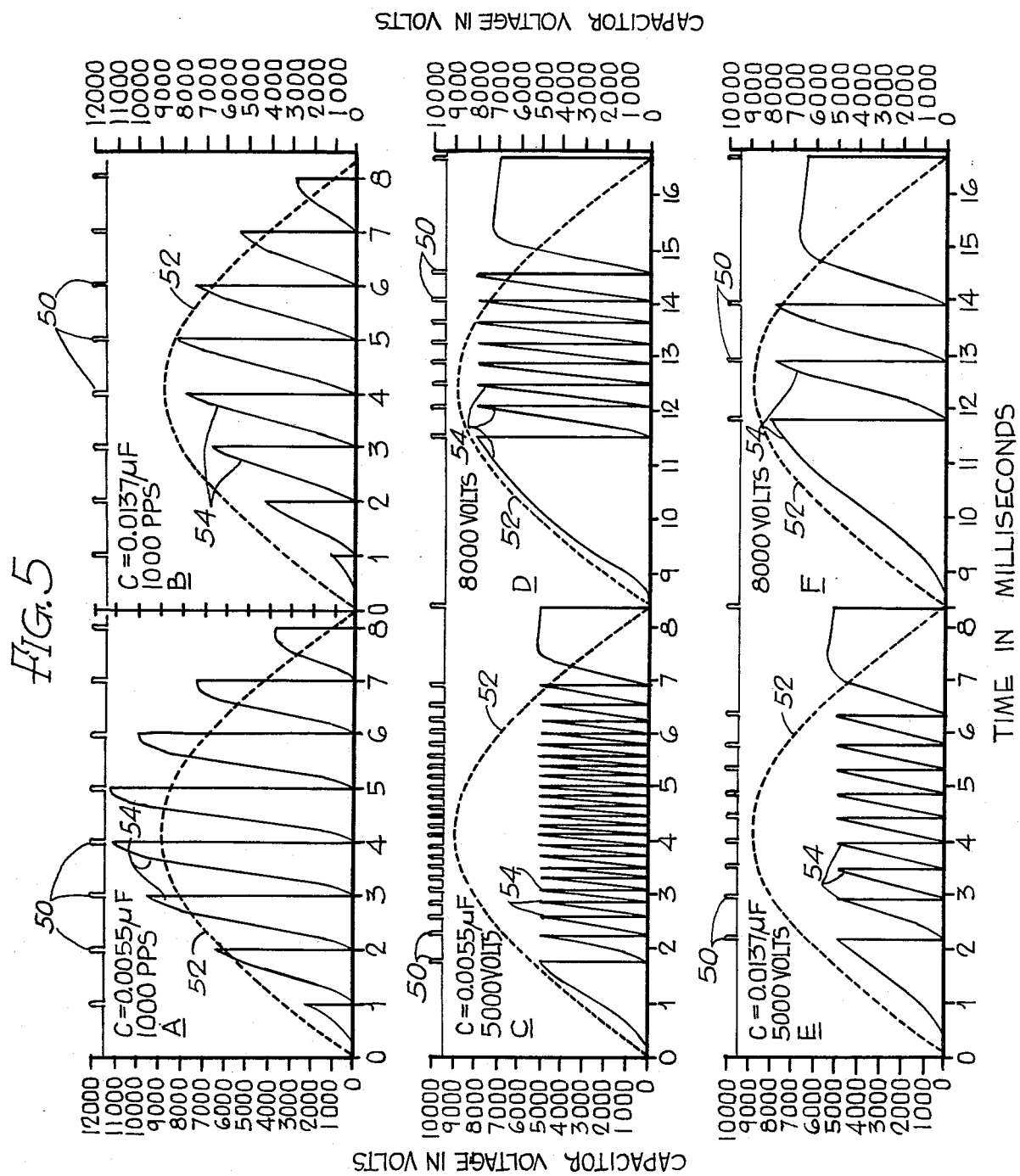
FIG. 5 is a series of waveform diagrams showing the effects of changes in the spark timing upon the magnitude of the voltage to which the capacitor is charged for each spark.

The effects of changes in the spark timing are graphically illustrated in FIG. 5. FIGS. 5A and B represent situations in which the spark triggering pulses are uniformly or equally spaced. Specifically, FIGS. 5A and B represent situations in which the spark triggering pulses are supplied at a repetition rate of 1000 pulses per second, so that the pulses are timed at intervals of 1 millisecond. Such evenly spaced pulses are represented at 50 in FIGS. 5A and B.

It will be understood that the high voltage transformer secondary T1S and the rectifier D1 supply rectified alternating current pulses, corresponding to half portions of a sine wave, as represented at 52 in FIGS. 5A-F. The half-period of the 60 cycle waveform amounts to about 8.3 milliseconds, so that each of the triggering pulses 50 is in a different relationship to the phase angle of the half-sinusoidal pulse 52.

Each triggering pulse 50 initiates the discharge of the capacitor C, which produces a spark across the spark gap G. The damped oscillatory capacitor discharge current, as represented by FIG. 10, dies out after a small fraction of a millisecond. The spark gap G then becomes nonconductive, with the result that the recharging of the capacitor C is commenced by the high voltage transformer T1, acting thorough the rectifier D1 and the resistor R1. The rate at which the capacitor C is recharged is directly related to the instantaneous voltage produced by the secondary winding T1S, and is inversely related to the inductance represented by LT, the resistance represented by R1 and the capacitance value of the capacitor C. The charging of the capacitor C continues until the next spark is triggered, or until the capacitor charging current attempts to reverse its direction, such reversal being prevented by the diode rectifier D1, so that the charge is retained on the capacitor C. Due to the presence of both inductance and capacitance in the charging circuit, the capacitor charging current tends to be oscillatory, so that the current rises to a peak, decreases to zero and tends to reverse, at which point the diode D1 prevents any such reversal. Due to the presence of both inductance and capacitance in the charging circuit, the capacitor charging voltage can rise to a value which is greater than the peak voltage developed by the secondary winding T1S of the high voltage transformer T1.

In FIG. 5, the waveform of the capacitor charging voltage is represented by the series of pulses 54, each of which rises gradually to a peak and then drops substantially to zero when the next spark is triggered by the next triggering pulse 50. For the situations represented by FIGS. 5A and B in which the triggering pulses 50 are evenly spaced at 1 millisecond intervals, the capacitor charging voltage pulses 54 are of unequal magnitude, due to the fact that each pulse 54 has a different relationship to the half-sinusoidal voltage waveform 52 developed by the secondary winding T1S, acting through the rectifier D1. The magnitude of the capacitor charging voltage pulses 54 depends directly upon the instantaneous voltage represented by the half-sinusoidal waveform 52 during the capacitor charging time span.

The capacitor charging voltage pulses 54 of FIG. 5A were developed with a capacitor value of 0.0055 microfarad. It will be seen that most of the capacitor voltage pulses 54 rise to a peak voltage which is greater than the instantaneous voltage developed during the charging time span by the transformer secondary T1S, as represented by the half-sinusoidal waveform 52.

In FIG. 5B, the capacitor charging voltage pulses 54 were produced with a higher capacitor value of 0.0137 microfarad, with the result that the voltage pulses 54 rose less rapdily to lower peak values than in the case of FIG. 5A. In both FIGS. 5A and B, each capacitor charging voltage pulse 54 has a different peak value, due to its uniquely different relationship to the half-sinusoidal voltage waveform 52.

FIGS. 5C, D, E and F illustrate the manner in which the spark timing may be varied, in accordance with the present invention, to cause the capacitor charging voltage pulses 54 to be constant or uniform in peak magnitude. It will be seen that in the waveform diagrams of FIGS. 5C–F, the timing of the spark triggering pulses 50 is nonuniform, so that the pulses 52 occur at unequal or variable intervals. These intervals are chosen or computed so that the capacitor voltage pulses 54 have the same magnitude, for each of the set of conditions represented by the individual waveform diagrams of FIGS. 5C–F.

The waveforms of FIG. 5C were produced with a storage capacitor C having a value of 0.0055 microfarad, the same as for FIG. 5A. However, the timing intervals of the triggering pulses 50 were varied to cause the peak voltage of the capacitor charging pulses 54 to be held constant at 5,000 volts. This was achieved by providing relatively large timing intervals between the triggering pulses 50 for the early and late portions of the half-sinusoidal transformer voltage waveform 52, while providing smaller time intervals between the triggering pulses 50 for intermediate portions of the half-sinusoidal waveform 52, when the instantaneous value of the half-sinusoidal waveform was at or near its maximum. Thus, more time was allowed for the capacitor C to charge when the instantaneous value of the rectified transformer voltage 52 was low, than when such rectified transformer voltage was high, so that the capacitor C was charged to the same voltage in all cases. Thus, the same energy was stored in the capacitor C to produce each of the sparks in the spark train.

In the case represented by FIG. 5D, the conditions remained the same as in FIG. 5C, except that the timing of the spark triggering pulses 50 was changed so as to raise the peak value of the capacitor charging pulses 54 to 8,000 volts. To achieve this higher voltage, the timing intervals between the triggering pulses 50 were increased, so that more time was allowed to charge the capacitor C in each instance. The time intervals were different from spark to spark, to allow for the different instantaneous values of the half-sinusoidal waveform 52, during the successive charging intervals of the capacitor C.

The waveform diagrams of FIG. 5E represent a condition in which the value of the capacitor C was increased to 0.0137 microfarad. The timing of the spark triggering pulses 50 was varied to maintain the peaks of the capacitor charging pulses 54 at 5,000 volts, as in the case represented in FIG. 5C. Because of the increased capacitance in the charging circuit, the intervals between the triggering pulses 50 were increased to allow more time for the capacitor to charge to the desired 5,000 volts. The individual intervals were adjusted to allow for the different instantaneous values of the half-sinusoidal transformer voltage waveform 52 during the successive intervals.

In the case represented by FIG. 5F, the capacitor value was the same as in the case of FIG. 5E, but the spark timing intervals were increased to raise the peak capacitor voltage to 8,000 volts. The timing of the individual intervals was varied to allow for the different instantaneous values of the half-sinusoidal waveform 52.

It will be evident from FIGS. 5C–F that the peak voltage to which the capacitor C is charged for each spark can be held constant by varying the timing of the sparks. The voltage to which the capacitor is charged can be raised by increasing the timing intervals between the sparks, so as to allow more time for the capacitor to charge. Conversely, the peak capacitor voltage can be decreased by decreasing the timing intervals between the sparks. If the value of the capacitor is increased, the timing intervals must be increased to maintain the same capacitor peak voltage, because more time will be required to charge the capacitor to the same voltage. The individual timing intervals between the sparks are adjusted to allow for the different instantaneous values of the half-sinusoidal voltage developed by the transformer.

It is usually desirable to charge the capacitor C to the same peak voltage for each spark in the spark train, as represented by the waveform diagrams of FIGS. 5C–F. For any particular value of capacitance, the energy stored in the capacitor C is a function of the voltage to which the capacitor is charged. Thus, if the capacitor is charged to the same voltage for each spark, the energy stored in the capacitor is the same, and the energy dissipated in each spark is the same. Accordingly, the total amount of light produced by each spark is the same. Moreover, the damped oscillatory capacitor discharge current, as represented by FIG. 10, has the same maximum amplitude and waveform for each spark. It follows that the maximum intensity of the light produced by each spark is the same. Moreover, the detailed structure of the spectrum produced by each spark is the same, because such detailed structure is determined by the maximum amplitude and waveform of the spark current, both of which stay the same, as represented, for example, by FIGS. 11 and 12.

Thus, the charging of the capacitor C to the same voltage for each spark makes it possible to achieve results which are fully repeatable and accurate.

Accordingly, with the present invention, spectral analyses can be carried out with a high degree of repeatability and accuracy.

FIG. 2 illustrates details of the timing control means 44 of FIG. 1. It will be seen that the timing control means 44 of FIG. 2 may utilize a computer 60, which may comprise a suitably programmed general purpose computer, or a special computer programmed solely to control the timing of the spark triggering pulses 50. The timing of the pulses is related to the instantaneous phase angle of the half-sinusoidal rectified transformer voltage 52 of FIG. 5. Accordingly, information with regard to such phase angle is fed into the computer 60. In this case, such information is developed by a zero-crossing detector 62, which receives an alternating current input from the power lines 18, through a switch 64. The zero-crossing detector 62 supplies a timing signal to the computer 60 whenever the alternating current waveform goes through zero. The computer 60 produces trigger control pulses at programmed or computed intervals after each zero-crossing signal. The interval between each pair of successive spark triggering pulses is programmed or computed to charge the capacitor C to the desired voltage, considering the instantaneous voltage which exists in the alternating current waveform during such interval. It is not necessary to feed the half-sinusoidal waveform 52, representing the rectified transformer secondary voltage, as shown in FIG. 5, directly to the computer 60, because the instantaneous magnitude of such waveform is a simple sine function of the phase angle, so that such instantaneous amplitude can readily be computed by the computer 60. The computer 60 can then compute the charging time which is needed to charge the capacitor C to the desired voltage, considering the existing values of the capacitor C, the inductance LT and the resistance R1 in the charging circuit. When the desired time interval has elapsed, the computer generates a control pulse to trigger the next spark. To assist the computer 60 in carrying out its timing functions, the computer may be connected to the output of a clock pulse generator 66, as shown in FIG. 2. It will be understood that the clock pulse generator 66 may be incorporated into the computer 60, if desired.

The trigger control pulses from the computer 60 are typically of small amplitude. As shown in FIG. 2, such pulses are fed to a trigger pulse generator 68 which produces corresponding spark triggering pulses of sufficient amplitude to trigger the thyratron 32 of FIG. 1. These pulses are fed to the control electrode of the thyratron 32 through the protective resistor R9.

FIG. 3 illustrates a modified construction which employs a half-wave rectifier circuit 70, instead of the full-wave bridge rectifier circuit of FIG. 1. As shown, the half-wave rectifier circuit 70 comprises only a single diode stack D1A. The other three diode stacks of FIG. 1 are omitted. As before, the diode stack D1A comprises a plurality of diode units D1U connected in series, with individual shunting resistors D1R of high value to equalize the distribution of the inverse voltage along the stack D1A. All of the previous discussion is applicable to the half-wave rectifier 70 of FIG. 3, except that the charging voltage is available during only alternate half-cycles of the alternating voltage from the high voltage transformer secondary T1S.

FIG. 4 illustrates a modified electronic switching circuit 72, in which an additional inductance unit L4 is connected in series with the anode-cathode path of the thyratron 32. Otherwise, the electronic switching circuit 72 is the same as illustrated in FIG. 1. The shunting diode rectifier D3 is connected across the thyratron 32 in the same manner as described and illustrated in FIG. 1.

The provision of the additional inductance element L4 in FIG. 4 is advantageous because it improves the commutation between the thyratron 32 and the shunting diode D3. It will be recalled that the thyratron 32 carries the capacitor discharge current in one direction, while the shunting diode D3 carries such current in the opposite direction. Thus, the thyratron 32 and the shunting diode D3 carry the oscillatory capacitor discharge current of FIG. 10 during alternate half-cycles, so that such current is commutated between the thyratron 32 and the shunting diode D3 at the transitions between such half-cycles. The inductance element L4 preferably has sufficient inductance to maintain a small current through the thyratron 32 during the half-cycles in which the shunting diode D3 is conductive. By maintaining such small current, the deionization of the thyratron 32 is prevented, so that the thyratron 32 is ready to conduct the main capacitor discharge current when such current reverses so that the shunting diode D3 is no longer conductive.

It may be helpful to offer a more detailed explanation of the action of the inductance element L4. During the half-cycles when the thyratron 32 carries the main capacitor discharge current, such current also passes through the inductance L4 and builds up a magnetic field around the inductance. When the main capacitor discharge current reverses, it switches to the shunting path through the shunting diode D3, because the thyratron 32 will not carry the reverse current. However, the magnetic field around the inductance L4 collapses and induces a continuing forward voltage in the inductance L4. Such forward voltage produces a continued forward current between the anode and the cathode of the thyratron 32. Such forward current circulates through the closed loop formed by the thyratron 32, the shunting diode D3 and the inductance element L4. If the inductance element L4 is large enough in inductance, the forward current through the thyratron 32 persists throughout the half-cycles when the main capacitor discharge current is being carried by the shunting diode D3. Thus, the thyratron 32 never deionizes, so that it is ionized and ready to carry the main capacitor discharge current when such current reverses so that it is switched from the shunting diode D3, back to the thyratron 32.

With the modified construction of FIG. 4, the commutation between the thyratron 32 and the shunting diode D3 is extremely smooth in both directions. In the absence of the inductance element L4, a commutation spike tends to be produced at the beginning of each half-cycle when the thyratron 32 carries the main capacitor discharge current, because a greater voltage is required across the thyratron to reionize the thyratron than to maintain the ionization after it has become conductive. The commutation spikes have the disadvantage of tending to cause radio frequency interference in other electronic and electrical equipment which happens to be near the spark source.

The provision of the inductance element L4 also has the advantage that the commutation between the thyratron 32 and the shunting diode D3 is always consistent and repeatable, even though the frequency of the damped oscillatory capacitor discharge current may vary over a wide range. There is no ambiguity of irregularity is such commutation, so that the waveform and duration of the damped oscillatory capacitor discharge current are free from any consequent ambiguities or irregularities.

It has been found that, in the absence of the inductance element L4, such ambiguities or irregularities are noticeable when the frequency of the oscillatory capacitor discharge current is such that the half-period of the oscillatory discharge current is of the same order of magnitude as the deionization time of the thyratron 32. For higher frequencies, when such half-period is substantially less than the deionization time, the thyratron 32 remains ionized during the half-cycles when the shunting diode D3 is carrying the main oscillatory capacitor discharge current. Thus, the thyratron 32 is still ionized when the main current switches back to the thyratron 32, so that the commutation is smooth and repeatable. For lower frequencies, when the half-period of the capacitor discharge current is substantially greater than the deionization time of the thyratron 32, the thyratron will always become deionized during the half-cycles when the shunting diode D3 is carrying the main capacitor discharge current. Thus, the thyratron 32 will always have to be reionized when the capacitor discharge current reverses so that it is switched back to the thyratron 32.

When the frequency of the oscillatory capacitor discharge current is such that its half-period is approximately equal to the deionization time of the thyratron 32, an ambiguous situation can arise in which the thyratron is sometimes deionized and sometimes not deionized, during the half-cycles when the shunting diode D3 is carrying the main capacitor discharge current. This ambiguous situation produces ambiguities and irregularities in the waveform and the total duration of the spark current, so that the spectroscopic results may not be fully repeatable. The ambiguities in the total duration of the spark current also produce ambiguities in the voltage to which the capacitor is subsequently recharged, because the recharging does not commence until the spark current dies out. Thus, any ambiguity in the total duration of the spark current produces a corresponding ambiguity in the time during which the capacitor is subsequently recharged, assuming that the timing of the sparks remains unchanged. The ambiguities in the charging time produce ambiguities in the charging voltage, which in turn produce ambiguities in the energy dissipated in the next spark, the total amount of light produced by the spark, the maximum amplitude of the spark current, the maximum amplitude of the light, the waveform of the spark current, the total duration of the spark current and the detailed structure of the spectrum produced by the spark.

Accordingly, it is highly desirable, particularly in the absence of the additional inductance element L4, to avoid using any combination of capacitance and inductance in the capacitor discharge circuit such as to produce an oscillatory half-period which is close to the deionization time of the thyratron 32.

In experiments using a hydrogen thyratron, Type 5C22, it has been found that the half-period of the oscillatory capacitor discharge current should be either less than 5 microseconds or more than 7 microseconds, to avoid ambiguities as to whether the thyratron is or is not deionized during the half-cycles when the main capacitor discharge current is carried by the shunting diode D3. Thus, the range of half-periods from 5 to 7 microseconds should be avoided for this thyratron, particularly if the inductance element L4 is not used. It will be understood that different thyratrons will have different deionization times. Moreover, the deionization time is subject to variations due to changes in the temperature of the thyratron and the pressure of the ionizable gas or vapor within the thyratron. In general, a range of half-periods which is close to the deionization time should be avoided.

The ambiguity as to whether or not the thyratron 32 is deionized can cause a significant ambiguity, on the order of 5 to 10%, in the total elapsed time of the spark current. The total elapsed time of the spark current is shortened when the thyratron is deionized during the half-cycles when the shunting diode D3 is conductive, because the reionization of the thyratron dissipates additional energy. Such loss of energy has an additional dampening effect upon the oscillatory capacitor discharge current.

The ambiguity of 5 to 10% in the total elapsed time of the oscillatory spark current can produce an ambiguity on the order of 10 to b 20% in the voltage to which the capacitor C is subsequently recharged. This ambiguity in the capacitor voltage can cause significant ambiguities in the total light produced by the spark, the maximum light intensity, and the detailed structure of the spectrum produced by such light.

FIG. 4 shows the further modification of inserting another inductance element L5 in series with the shunting diode D3. The provision of the inductance element L5 has the advantage of producing additional improvement in the commutation between the thyratron 32 and the shunting diode D3. The inductance element L5 is preferably adjusted to an inductance value which is large enough to maintain a small current in the shunting diode D3 when the thyratron 32 is carrying the main capacitor discharge current. Thus, the shunting diode D3 is kept conductive so that it is ready to carry the main capacitor discharge current when it passes through zero and reverses so that the current is switched away from the thryratron 32 to the diode D3.

When the diode D3 is carrying the main capacitor discharge current, the current also flows through the inductance element L5, so that a magnetic field is built up around the inductance element L5. When the main discharge current reverses and is switched to the thyratron 32, the magnetic field around L5 collapses gradually and induces a voltage which causes current to flow around the closed loop comprising the diode D3, the inductance element L5, the inductance element L4 and the thyratron 32.

The provision of the inductance element L5 has the advantage of obviating the production of any commutation spikes when the diode D3 starts to carry the main capacitor discharge current. Thus, the radio frequency interference which might otherwise be caused by such spikes is obviated. Moreover, the provision of the inductance element L5 results in a further improvement in the smoothness and repeatability of the commutation between the diode D3 and the thyratron 32, despite wide variations in the frequency of the oscillatory capacitor discharge current.

The inductance elements L4 and L5 are preferably variable so that they can be adjusted to suit a variety of operating conditions. However, fixed values of inductance may also be employed.

The effect of the spark timing upon the capacitor charging voltage has already been described with reference to FIG. 5. FIGS. 6-9 illustrate the manner in which the capacitor charging voltage and current are affected by the spark timing and various other factors, including variations in the capacitance of the capacitor C, the effective charging inductance LT and the effective charging resistance R1.

Figure 6:
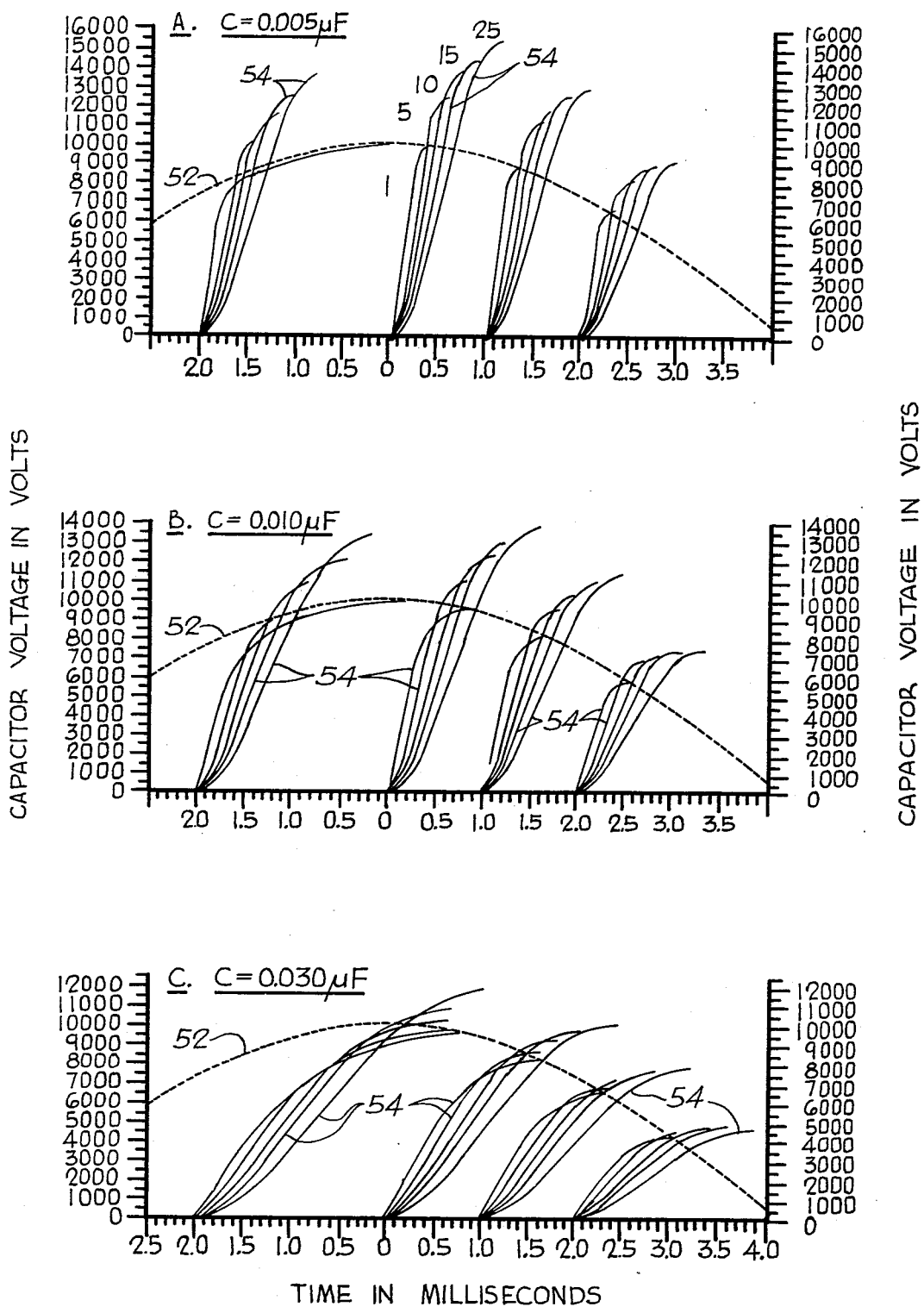
FIG. 6 is a series of waveform diagrams showing the charging of the capacitor for different values of the spark timing, the capacitance of the capacitory, and the inductance in the charging circuit.

FIG. 6 again shows the half-sinusoidal waveform 52 of the rectified alternating voltage from the transformer secondary T1S and the rectifier D1. FIG. 6 also shows several sets of graphs representing the waveform 54 of the capacitor charging voltage for various conditions. The graphs of FIG. 6A were produced with the storage capacitor C adjusted to a value of 0.005 microfarad. Four different families of graphs were produced for four different spark ignition times: 0, −2.0 milliseconds, +1.0 millisecond, and +2.0 milliseconds, where 0 represents the time at which the half-sinusoidal waveform 52 is at its peak value. For each spark ignition time, the effective charging inductance LT was adjusted to five different values: 1, 5, 10, 15 and 25 millihenrys. It will be seen that the peak voltage to which the capacitor C is charged increases with the increasing inductance. For the higher values of inductance, the capacitor C is charged to a voltage which is substantially greater than the peak of the supply voltage 52. The timing of the spark ignition has a very significant effect upon the peak voltage to which the capacitor C is charged. When the half-sinusoidal waveform 52 is high during the capacitor charging interval, the capacitor is charged to a relatively high voltage, and vice versa. When the capacitor C has been charged to its peak value of voltage, the diode rectifier D1 prevents the discharge of the capacitor through the charging circuit.

The graphs of FIGS. 6B and C were produced with different values of capacitance: 0.010 microfarad and 0.030 microfarad, respectively. The same four families of graphs were produced by varying the spark ignition times and the charging inductance LT, as explained in connection with FIG. 6A. It will be seen that increasing the value of the capacitor C had the effect of decreasing the peak voltage to which the capacitor was charged, in virtually all cases. The time required to charge the capacitor to its peak value was increased, as the value of the capacitor was increased.

It will be seen from FIG. 6 that, for a spark repetition rate of 120 sparks per second, the peak capacitor voltage can be adjusted over a wide range by changing the timing of each spark with respect to the half-sinusoidal waveform 52. Much greater repetition rates can be achieved, if desired, as discussed in connection with FIG. 5.

Figure 7:
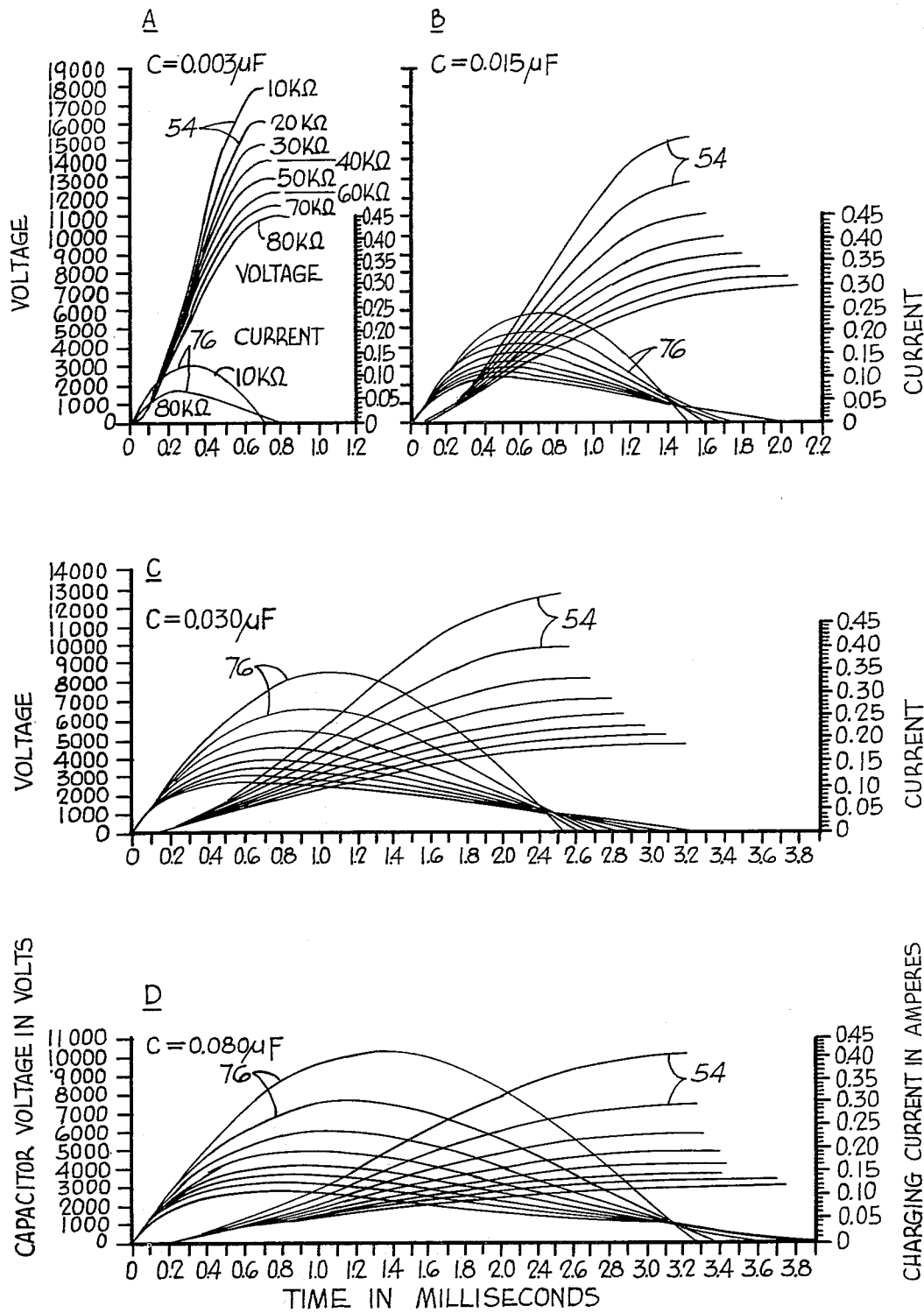
FIG. 7 is a series of waveform diagrams showing the capacitor charging voltage and the capacitor charging current for different values of capacitance and resistance in the charging circuit.

FIG. 7 illustrates the capacitor charging voltage waveform 54 for various values of the charging resistance R1. FIG. 7 also illustrates the waveform of the capacitor charging current 76. The spark timing was the same for all of the graphs in FIG. 7.

The graphs of FIG. 7A were produced with the capacitor C adjusted to a capacitance value of 0.003 microfarad. A family of graphs was produced with eight different values of the charging resistor R1, 10K, 20K, 30K, 40K, 50K, 60K, 70K, and 80K ohms. The spark ignition time was zero in all cases. It will be seen that the peak voltage to which the capacitor C is charged is reduced by increasing the charging resistance. Moreover, the total charging time is increased. The charging current, as represented by the waveform 76, is also reduced as the charging resistance is increased.

The graphs of FIGS. 7B, C and D were produced with three different values of capacitance: 0.015 microfarad, 0.030 microfarad, and 0.080 microfarad. In all cases, the spark ignition time was kept at zero. Families of graphs were produced for the eight different values of the charging resistance R1, as explained in connection with FIG. 7A. It will be seen that increasing the value of the capacitor C1 had the effect of decreasing the peak voltage to which the capacitor was charged. The total charging time was increased. Increasing the value of the capacitor C had the effect of increasing the capacitor charging current, as represented by the waveform 76. In all cases, the capacitor charging voltage and current were reduced by increasing the charging resistance R1.

FIG. 7 clearly indicates that the charging of the capacitor tends to be an oscillatory process, in that the charging current 76 rises to a peak and then decreases to zero. However, the diode rectifier D1 prevents the charging current from reversing, and prevents the capacitor C from being discharged through the charging circuit. The peak of the voltage waveform 54 is reached when the current waveform 76 drops to zero after passing through its peak.

FIGS. 8 and 9 illustrate the effects of varying the values of the capacitor C and the charging inductance LT. The graphs of FIGS. 8 and 9 show the capacitor charging voltage waveform 54 and current waveform 76. The graphs of FIG. 8 were produced for a capacitance value of 0.003 microfarad, a charging resistance value of 20K ohms, and a peak rectified transformer voltage of 10,000 volts. The spark ignition time was 0, corresponding to the peak of the rectified transformer voltage. The graphs were produced for nine different values of the charging inductance LT: 1, 3, 5, 10, 20, 50, 100, 200 and 500 millihenrys.

It will be seen from FIG. 8 that increasing the charging inductance decreases the peak charging current to the capacitor C. The total charging time is increased. As the charging inductance is increased, the peak capacitor charging voltage is increased at first, but then is decreased, due to the fact that the half-sinusoidal transformer voltage is decreasing during the increased charging time. In each case, the capacitor charging current 76 rises to a peak and then decreases to zero. The maximum capacitor voltage is achieved when the charging current falls to zero. The diode rectifier D1 prevents the discharge of the capacitor through the charging circuit, and prevents the reversal of the charging current after it drops to zero.

The graphs of the capacitor voltage 54 and the capacitor charging current 76 of FIG. 9 were produced for an increased value of capacitance: 0.010 microfarad. The values of the charging resistance and the peak transformer voltage were the same as for FIG. 8. The graphs 54 and 76 were produced for seven different values of the charging inductance LT: 1, 3, 5, 10, 20, 50 and 100 millihenrys. The peak values of the charging current 76 were increased, due to the increased capacitance. The peak values of the capacitor voltage were decreased. Moreover, the total charging times were increased, due to the increased capacitance. With increasing inductance, the total charging time increased. The peak charging voltage increased at first, and then started to decrease, due to the decrease in the half-sinusoidal transformer voltage with increasing charging time.

The spark sources of FIGS. 1 and 3 utilize a single phase high voltage transformer T1. The construction of FIG. 1 utilizes a full-wave bridge rectifier D1, while the construction of FIG. 3 employs a half-wave rectifier 70. Other variations are possible. For example, a three-phase transformer array may be employed in conjunction with a three-phase diode bridge utilizing 12 diode stacks.

As previously indicated, the timing control means 44 of FIGS. 1 and 2 may be constructed to time the spark triggering pulses so that the capacitor C is charged to the same voltage for all of the sparks in a spark train. It is also possible to charge the capacitor C to different voltages for different sparks, in accordance with any desired program or scheme.

As previously mentioned in connection with FIGS. 1 and 2, the frequency of the oscillatory capacitor discharge current can be varied over a wide range by changing the value of the capacitor C and by adjusting the inductances of the inductance coils L1 and L2. At relatively high frequencies, the half-period of the oscillatory capacitor discharge current will be less than the deionization time of the thyratron 32, so that the thyratron 32 will remain ionized and conductive during the half-cycles when the shunting diode D3 is carrying the capacitor discharge current. At relatively low frequencies, the half-period of the oscillatory capacitor discharge current will be substantially greater than the deionization time of the thyratron 32, so that the thyratron will become deionized and nonconductive during the half-cycles when the shunting diode D3 is carrying the capacitor discharge current. Thus, the thyratron 32 will have to be refired when the capacitor discharge current reverses so that it must again be carried by the thyratron. The extra energy required to refire the thyratron has the effect of reducing the total length of each spark discharge, so that the recharging of the capacitor C is initiated earlier than is the case when the thyratron remains ionized. This earlier initiation of the capacitor recharging process increases the voltage to which the capacitor is recharged, above the voltage that is produced when the thyratron does not become deionized. Thus, the calibration of the computer employed in the timing control means needs to be different for the two cases, when the thyratron is deionized or is not deionized during the half-cycles when the shunting diode D3 is conductive. This ambiguous calibration can be avoided by introducing a sufficiently large inductance L4 in series with the thyratron 32, so as to keep a small current flowing in the thyratron during the half-cycles when the shunting diode D3 is conductive.

The shunting diode D3, where preferably comprises a stack of solid-state diode units D3U, has a charge dissipation time which is analogous in a general way to the deionization time of the thyratron 32. However, the charge dissipation time is considerably less than the deionization time. Thus, the charge dissipation time is not likely to cause errors or ambiguities, unless the oscillatory frequency of the capacitor discharge current is extremely high. Moreover, the charge dissipation time of any particular solid-state device is generally dependent solely on its temperature, which can be controlled by cooling the solid-state device. Any ambiguity due to charge dissipation time can be avoided by introducing a sufficient inductance L5 is series with the diode D3, as described in connection with FIG. 4.

The deionization time of the thyratron 32 is the most significant factor which may cause uncontrolled variations in the total duration of each spark discharge. However, any other uncontrolled variations in the capacitor discharge circuit should be avoided because such variations may affect the total duration of each spark discharge. Such uncontrolled variations may include, for example, changes in the capacitance, inductance and resistance of the various circuit components due to temperature changes.

It has been found that the timing of the spark triggering pulses can be calculated by the computer within an accuracy of about 10%. The factors involved in the computation are the capacitance, inductance and resistance in the capacitor charging circuit, and also the magnitude of the high alternating voltage developed in the transformer secondary winding T1S. From these factors, the computer is able to calculate the capacitor voltage which will be achieved with any given timing of the spark, or the timing which must be employed to achieve any particular capacitor voltage. It has been found than the answer to either of these questions can be calculated to an accuracy of about 10%. Final adjustments are made empirically. However, these final adjustments are small. The empirical adjustment is made by actually measuring the capacitor voltage which is achieved with a particular timing. If the capacitor voltage is greater or less than the desired value, the timing is retarded or advanced until the desired capacitor voltage is achieved.

A wide range of adjustment can be achieved by the timing control. A minimum voltage is required to produce the proper operation of the thyratron 32. It has been found that this minimum voltage amounts to 2,000 or 3,000 volts for hydrogen thyratrons. The upper limit of the voltage is about two times the peak voltage E developed by the transformer secondary winding T1S. A typical control range is from about 0.5E to about 1.5E, or a range of about 3 to 1. This is an adequately wide range, particularly when translated into the corresponding range of coulombs stored in the capacitor C. The total amount of light produced by the spark is proportional to the coulombs stored. The amount of material sampled from the electrodes is also proportional to the coulombs.

The wide ranging control afforded by the spark timing makes it possible to construct a servo system in which the spark source is servoed by the photoelectric analytical signal developed by the spectrometer which utilizes the light produced by the sparks. If not enough light is produced, the magnitude of the analytical signal will be blow normal. The analytical signal may be fed to the computer with a programming to cause the computer to change the spark timing so as to increase the amount of light to the desired value.

By controlling the spark timing, the computer can control not only the peak capacitor charging voltage and the area under the curve of the spark discharge current, but also the peak to valley ratio of the spark discharge current waveform. The mass of the material eroded from the electrodes is proportional to the area under the curve. The peak to valley ratio changes the detailed structure of the spectra produced by the light source, because elements of different atomic mass are affected differently by the changes in the peak to valley ratio. Such ration is affected by the value of the inductance L2 in series with the spark gap, and also by the peak current which flows initially through such inductance, because these two factors determine the energy which is stored in the magnetic field of the inductance.

Figure 13:
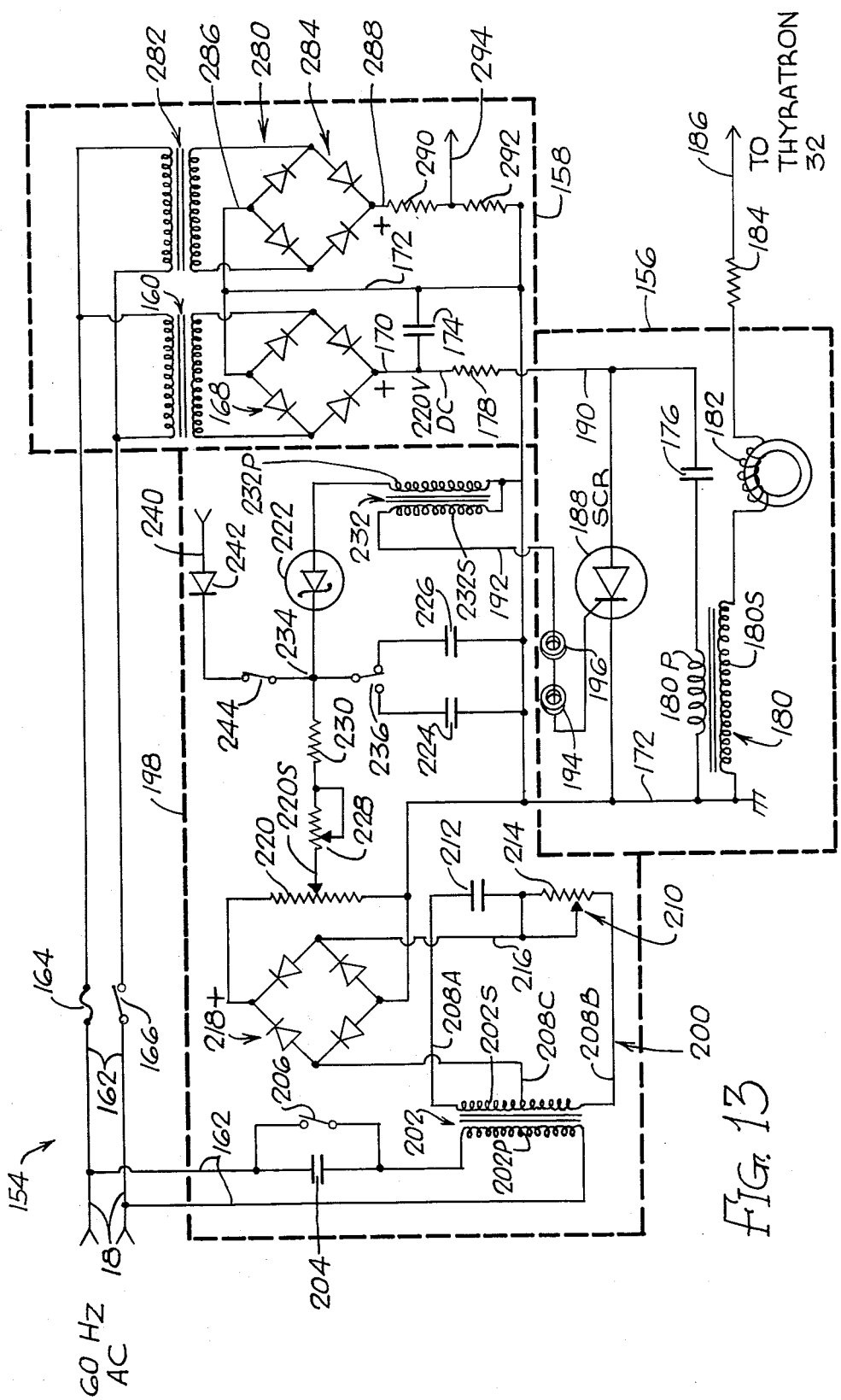
FIGS. 13 and 14 are schematic circuit diagrams showing modified timing control means.
Figure 14:
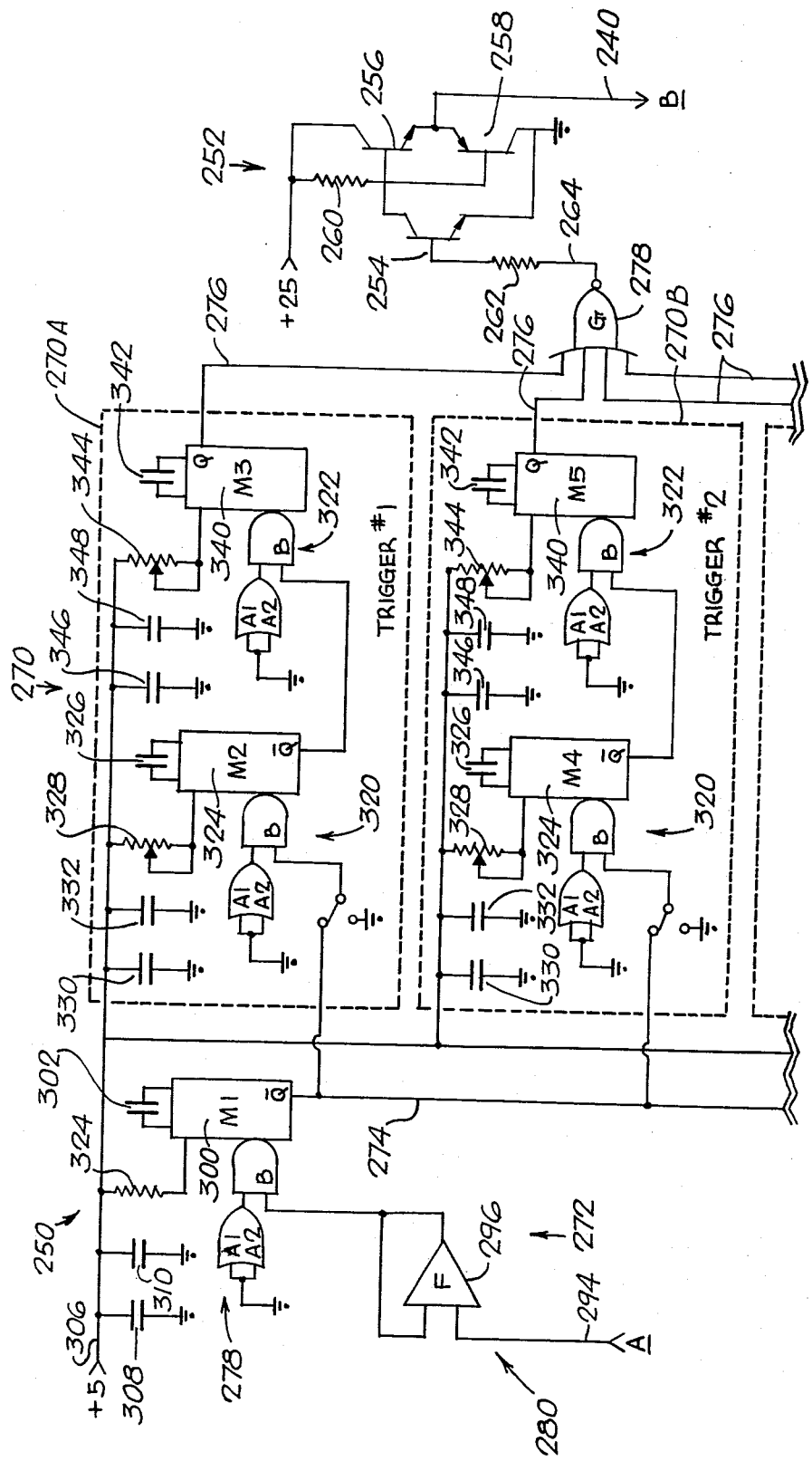

FIGS. 13 and 14 illustrate another modified construction for the timing control means 44 of FIGS. 1 and 2, such modified construction being designated 154. As shown in FIG. 13, the timing control means 154 include a triggering circuit 156 for producing pulses of sufficient magnitude to trigger the thyratron 32 of FIG. 1 into a conductive state. The triggering circuit 156 derives its operating power from a power supply 158. As shown, the power supply 158 comprises a power transformer 160 having its primary winding connected to alternating current supply lines 162. A fuse 164 and a switch 166 are connected in series with the power lines 162. The power transformer 160 has its secondary winding connected to the input terminals of a bridge rectifier 168 having positive and negative output terminals or leads 170 and 172. A filtering capacitor 174 is connected between the leads 170 and 172, which may supply direct current at about 220 volts, or any other suitable voltage.

In the triggering circuit 156, the direct voltage from the power supply 158 is employed to charge a capacitor 176, one side of which is connected to the positive power supply lead 170 through a current-limiting resistor 178. The other side of the capacitor 176 is connected through the primary winding 180P of a step-up pulse transformer 180 to the negative lead 172, which may be grounded. The capacitor 176 is charged through the resistor 178 and the primary winding 180P.

The pulse transformer 180 has a high voltage secondary winding 180S, one side of which is grounded to the lead 172. The other side of the secondary winding 180S is connected through an inductance element 182 and a resistor 184 to a lead which is adapted to be connected to the control electrode of the thyratron 32, shown in FIG. 1.

In the triggering circuit 156 of FIG. 13, the capacitor 176 is adapted to be discharged by a control element, illustrated as a silicon controlled rectifier (SCR) 188 having its negative electrode connected to the grounded lead 172. The positive electrode of the SCR is connected to a lead 190 which forms the junction between the capacitor 176 and the charging resistor 178. When the SCR 188 becomes conductive, the capacitor 176 is abruptly discharged through the SCR and the primary winding 180P. This discharge produces a high voltage pulse in the secondary winding 180S, such high voltage pulse being employed to fire the thyratron 32 into a conductive state. The discharge current of the capacitor 176 is slightly oscillatory, to insure that the SCR 188 will not latch in a conductive state.

In FIG. 13, the triggering circuit 156 has an input lead or terminal 192, connected through small inductance elements 194 and 196 to the control electrode of the SCR 188. Pulses of variable timing may be supplied to the input lead 192 by a timing circuit 198 having internal means for producing pulses at a repetition rate of 120 or more per second, related in phase to the 60 Hertz alternating current from the power supply lines 162. The timing circuit 198 includes means for varying the phase relationship between the pulses and the 60 Hertz alternating current.

The timing circuit 198 of FIG. 13 includes phase reference means 200 to refer the phase of the timing output pulses to the phase of the 60 Hertz alternating current from the supply lines 162. It will be recalled that the rectified high-voltage pulses employed to charge the main capacitor C in the spark discharge circuit 10 are also referred in phase to the 60 Hertz alternating current from the supply lines 18, to which the supply lines 162 are connected. Thus, the phase of the timing pulses from the timing circuit 198 is effectively referred to the phase of the rectified high-voltage pulses employed to charge the capacitor C.

In FIG. 13, the phase reference means 200 include a transformer 202 having its primary winding 202P connected to the alternating current supply lines 162, which in turn are connected to the main alternating current supply lines 18. A phase shifting capacitor 204 is connected in series with one of the leads to the primary winding 202P. A switch 206 is provided to short-circuit the capacitor 204 when the phase shifting action of the capacitor is not needed.

The transformer 202 has a secondary winding 202S with end leads 208A and B and a center tap 208C. A phase shifting circuit 210 is connected to the secondary winding 202S. As shown, the phase shifting network 210 comprises a capacitor 212 and a variable resistor 214 connected in series between the end leads 208A and B of the secondary winding 202S. An output voltage of variable phase is produced between the center tap 208C and a lead 216 connected to the junction between the capacitor 212 and the variable resistor 214. By varying the resistor 210, the phase of the 60 Hertz voltage between the leads 208C and 216 can be varied through a phase angle range of nearly 180°.

The variable phase voltage between the leads 208C and 216 is rectified by a full-wave bridge rectifier 218 which supplies its rectified and pulsating output to a potentiometer 220. The negative output terminal of the bridge rectifier 218 is connected to the grounded lead 172. The potentiometer 220 has a slider 220S for adjusting the magnitude of the pulsating direct voltage between the slider 220S and the grounded lead 172.

The pulsating direct voltage from the slider 220S is converted into abrupt pulses by a pulse forming circuit utilizing a trigger element 222, which is illustrated as a breakdown diode, such as a diode of the four layer type. Either of two capacitors 224 and 226 is charged through resistors 228 and 230, and then is discharged through the diode 222 and the primary winding 232P of a pulse transformer 232. The capacitor discharge produces a high voltage pulse in the secondary winding 232S of the transformer 232. One side of the secondary 232S is grounded to the lead 172, while the other side is connected to the input lead 192 which extends to the control electrode of the SCR 188.

In FIG. 13, the charging resistors 228 and 230 are connected in series between the slider 220S and a junction lead 234. A two-position switch 236 is connected between the junction lead 234 and the capacitors 224 and 226. The capacitors 224 and 226 are connected to the fixed contacts of the switch 236, the movable contact being connected to the junction lead 234. One side of each of the capacitors 224 and 226 is grounded to the lead 172. The switch 236 makes it possible to change the time constant of the charging circuit comprising the resistors 228 and 230 and the capacitors 224 and 226. The resistor 228 is variable to provide an adjustment of the time constant.

The breakdown diode 222 is connected in series with the primary winding 232P between the junction 234 and ground.

In FIG. 13, the switch 236 is shown in its position in which the capacitor 226 is in the circuit. During each rectified pulse from the slider 220S of the potentiometer 220, the capacitor 226 is charged through the resistors 228 and 230. When the capacitor 226 becomes charged to the breakdown voltage of the diode 222, the diode breaks down abruptly and becomes conductive, so that the capacitor 226 is discharged abruptly through the primary winding 232P. The discharge current pulse produces a high voltage pulse in the secondary 232S. Such high voltage pulse fires the SCR 188, so that it becomes conductive.

The capacitor 176 is then discharged through the SCR 188 and the primary winding 180P. The discharge current pulse produces a high voltage pulse in the secondary 180S. Such high voltage pulse fires the thyratron 32 of FIG. 1, so that the main capacitor C is discharged across the spark gap G.

The potentiometer 220 and the variable resistor 228 can readily be adjusted so that one or more trigger pulses will be produced for each rectified pulse from the bridge rectifier 218. For a 60 Hertz alternating current supply, there will be 120 or more rectified pulses per second. Accordingly, the timing circuit 198 will produce 120 or more timing pulses per second. The timing of these pulses can be adjusted, relative to the phase of the rectified pulses, by adjusting the potentiometer 220 and the variable resistor 228. For example, the timing can be adjusted so that each timing pulse will occur at the peak of the corresponding rectified pulse. Other timing adjustments can also be employed.

After the capacitor 224 or 226 has been discharged through the breakdown diode 222, the diode again becomes nonconductive, so that the capacitor will again be charged during the next rectified voltage pulse. Thus, the timing circuit 198 normally produces 120 timing pulses per second when operating under internal control. The phasing of these pulses can be adjusted by varying the resistor 214, which provides an adjustment of the phase angle of the alternating voltage through nearly 180°. An additional change in phase can be produced by opening the switch 206 so as to introduce the capacitor 204 into the primary circuit of the transformer 202. Thus, the timing pulses produced by the timing circuit 198 can be adjusted into any desired phase relationship with the rectified high voltage pulses employed to charge the main spark discharge capacitor C.

The timing circuit 198 also includes a provision for external control. Thus, in FIG. 13, an input lead 240 is connected to the junction 234 through a diode 242 and a switch 244. When external control is desired, the switch 244 is closed. The potentiometer 220 is also generally adjusted to zero, or the transformer primary 202P is disconnected from the alternating current supply lines 162.

FIG. 14 illustrates an external control timing circuit 250 for supplying one or more timing pulses to the external control lead 240 during each of the 120 rectified pulses. Provision is made for individually timing each of the timing pulses during each rectified pulse. The external timing pulses break down the diode 222 in FIG. 13 and produce current pulses in the primary winding 232P, so that the SCR 188 is fired. This, in turn, fires the thyratron 32 of FIG. 1.

In FIG. 14, the external timing control circuit 250 includes an output amplifier 242 to produce output pulses of a sufficient magnitude. Amplifiers of various types may be employed. The illustrated amplifier 252 employs three transistors 254, 256 and 258 in a "totem pole" circuit which also utilizes a biasing resistor 260 and an input resistor 262. Timing pulses of relatively small magnitude can be supplied to the input lead 264 of the amplifier 252.

In FIG. 14, the individual timing pulses are produced by individual trigger circuits 270. Two such trigger circuits 270A and B are illustrated, but any desired number of trigger circuits may be provided, corresponding to the number of timing pulses which are desired for each of the 120 rectified alternating current pulses. Each trigger circuit 270 can be adjusted to control the exact timing of its output pulse, with respect to a common input pulse, which is phase locked to the 60 Hertz alternating current supply, and thus to the rectified high voltage pulses supplied to the main spark capacitor C of FIG. 1. The common input pulse in produced by a phase locking circuit 272 in FIG. 15 and is supplied to the trigger circuits 270 by a common lead 274.

The trigger circuits 270 have individual output leads 276 which are coupled to the input lead 264 by a multiple NOR gate 278. Any suitable number of such gates may be employed to provide enough inputs for all of the trigger circuits 270.

The phase locking circuit 272 of FIG. 14 includes reference means 280 for referring the input of the circuit to the phase of the alternating current supply, such reference means being shown partly in FIG. 13 and partly in FIG. 14. Thus, in FIG. 13, such reference means include an additional transformer 282 having its primary winding connected to the alternating current supply lines 162, which in turn are connected to the main supply lines 18. The transformer 282 has its secondary winding connected to a full-wave bridge rectifier 284 with output leads 286 and 288. The negative output lead 286 is grounded to the lead 172, while the positive lead 288 is connected to a voltage divider, comprising resistors 290 and 292 connected in series between the lead 288 and ground. A lead 294 is connected to the junction between the resistors 290 and 292. The lead 294 also appears in FIG. 14 and is operative to supply rectified alternating pulses to the phase locking circuit 272.

In FIG. 14, the phase reference means 280 may include a follower amplifier 296 having its input connected to the lead 294. The output of the amplifier 296 is connected to pulse generating means 298 for producing brief pulses of uniform amplitude, corresponding to zero points of the rectified pulses from the amplifier 296.

The illustrated pulse generator 298 utilizes a monostable multivibrator 300, preferably in the form of an integrated circuit. The B input of the monostable 300 is connected to the output of the amplifier 296. The duration of each pulse produced by the monostable 300 is determined by a timing capacitor 302 and a timing resistor 304, connected to the monostable, the resistor 304 being connected between the monostable and a power supply line 306. Bypass capacitors 308 and 310 are connected between the supply line 306 and ground.

The phase locking circuit 272 functions as a zero crossing detector, to produce a brief pulse corresponding to each zero crossing of the alternating current supply. Such pulse is supplied to the output lead 274 which is connected to the input of each of the trigger circuits 270.

All of the trigger circuits 270 may be the same, except for adjustment, so that it will suffice to describe the first trigger circuit 270A. In general, the trigger circuit 270A comprises a timing or delay circuit 320 and a pulse duration circuit 322. The timing or delay circuit 320 and a pulse duration circuit 322. The timing or delay circuit determines the timing of each output pulse produced by the trigger circuit 270A, relative to the reference provided by the corresponding input pulse. The duration circuit 322 determines the duration of each output pulse.

In FIG. 14, the timing or delay circuit 320 utilizes a monostable 324 having a timing capacitor 326 and a timing resistor 328, the resistor being connected between the monostable and the power supply lead 306. The resistor 328 is variable so that the duration of the monostable output pulse can be adjusted. Bypass capacitors 330 and 332 are connected to a supply lead 306.

A two-position switch 334 is connected between the input pulse supply lead 274 and the B input of the monostable 324, the movable contact of the switch 334 being connected to the B input. One fixed contact is connected to the lead 274, while the other fixed contact is grounded, so that the trigger circuit 270A can be inactivated by operating the switch 334 so that the B input will be grounded.

The duration of the output pulse from the monostable 324 determines the delay in the production of the output pulse from the trigger circuit 270A. The duration circuit 322 determines the duration of the output pulse from the trigger circuit 270A.

As shown in FIG. 14, the duration circuit 322 utilizes another monostable 340 having its B input connected to the output of the monostable 324. Thus, the monostable 340 develops an output pulse corresponding to the trailing edge of the output pulse from the monostable 324. The monostable 340 has a timing capacitor 342 and a timing resistor 344 which determine the duration of the pulse produced by the monostable 340, the resistor 344 being connected between the monostable and the power line 306. Bypass capacitors 346 and 348 are connected between the power line 306 and ground. The pulse output line 276 of the trigger circuit 270A is connected to the Q output of the monostable 340.

In operation, the phase locking circuit 272 produces a brief pulse corresponding to each zero crossing of the alternating current from the supply lines 18. The output pulses from the phase locking circuit 272 are supplied to all of the trigger circuits 270. There may be any desired number of the trigger circuits 270. Each trigger circuit 270 produces a single output pulse in response to each input pulse. The timing of each output pulse is adjustable by varying the resistor 328. The trigger circuits 270 are adjusted so that the respective output pulses are produced sequentially at the desired time intervals during each half cycle of the alternating current supply. The timing of each output pulse determines the magnitude of the corresponding spark discharge. It is generally desirable that all of the spark discharges be substantially the same in magnitude. The timing of each output pulse from the trigger circuits 270 can be adjusted to bring this about.

This adjustment can be brought about by connecting the input of an oscilloscope, or some other voltage indicator, to the spark discharge circuit of FIG. 1, so as to display the capacitor charging voltage of the main capacitor C or the spark current across the spark gap G. The timing resistors 328 can then be adjusted sufficiently for the successive trigger circuits 270, so that the successive spark discharges are all the same in magnitude. There is no serious difficulty in carrying out this series of adjustments.

Alternatively, the timing of each spark triggering pulse can be calculated, as previously discussed, with or without the aid of a computer, on the basis of the various parameters of the spark discharge circuit of FIG. 1. Such parameters include the capacitance of the main capacitor C, the charging inductance represented by LT, the resistance represented by R1, the alternating voltage developed by the transformer T1, the capacitor voltage to be maintained, and the duration of each spark discharge.

For those who wish to employ a computer to make these calculations, a computer program is available to the public at the computer center of the University of Wisconsin in Madison, Wisconsin. Access to this computer program can be obtained by anyone having a standard teletypewriter computer terminal. Such computer program is designated OLD LCR2. This computer program makes it possible for the computer to compute the timing of the spark triggering pulses in order to produce any particular voltage across the main charging capacitor C for each spark discharge. Conversely, it is possible to compute the capacitor charging voltage for each spark discharge, if the timing is given.

Those skilled in the art will be able to assign appropriate values and type designations to the various components of the electrical circuits disclosed herein. However, it may be helpful to offer the following component value and type designations which have been employed successfully in actual tests. It will be understood that these component values and type designations may be varied widely to suit various operating conditions.

| CAPACITORS | |
|---|---|
| CAPACITOR | VALUE IN MICROFARADS OR PICOFARADS (Pf) |
| 174 | 8. |
| 176 | 0.002 |
| 204 | 0.22 |
| 212 | 1. |
| 224 | 0.015 |
| 226 | 0.015 |
| 308 | 3. |
| 310 | 50. Pf. |
| 302 | 100. Pf. |
| 326 | 0.015 |
| 330 | 3. |
| 332 | 50. Pf. |
| 342 | 0.015 |
| 346 | 3. |
| 348 | 50. Pf. |

| RESISTORS | |
|---|---|
| RESISTORS | VALUE IN OHMS |
| 178 | 2.7 k |
| 184 | 100. |
| 214 | 10. k |
| 220 | 10. k |
| 228 | 300. k |
| 230 | 10. k |
| 262 | 18. k |
| 264 | 1.5 k |
| 290 | 1000. |
| 292 | 1000. |
| 324 | 10. k |
| 328 | 10. k |
| 344 | 1. k |

| INDUCTORS | |
|---|---|
| INDUCTOR | TYPE |
| 182 | Ferrite bead. |
| 194 | Ferrite bead. |
| 196 | Ferrite bead. |

| SOLID STATE COMPONENTS | |
|---|---|
| COMPONENT | TYPE |
| 188 | 2N4333 Motorola SCR. |
| 222 | 1N5160 Motorola 4-layer diode. |
| 254 | 2N3904 Motorola transistor. |
| 256 | 2N3904 Motorola transistor. |
| 258 | 2N3906 Motorola transistor. |
| 278 | SN7423 Dual Quad-input NOR gate. |
| 296 | μA742C |
| 300 | 74121N Monostable multivibrator. |
| 324 | 74121N Monostable multivibrator. |
| 340 | 74121N Monostable multivibrator. |

We claim:
1. A spark source, comprising
a high voltage transformer having a secondary winding for supplying alternating current at a high voltage,
a storage capacitor,
a charging circuit including a rectifier connected between said secondary winding and said capacitor for charging said capacitor,
spark gap electrodes having a spark gap therebetween,
a discharge circuit including an electronic switching device connected between said capacitor and said spark gap electrodes for discharging said capacitor across said spark gap,
said electronic switching device having input means for receiving triggering signals,
and control means for supplying a sequence of variably spaced triggering pulses to said input means for producing a sequence of spark cycles in which said capacitor is charged to substantially equal voltages for all of said spark cycles,
said control means including variable timing means responsive to the phase angle of the alternating current supplied to said high voltage transformer for varying the timing of each triggering pulse in response to the phase angle variation of the alternating current during the interval subsequent to the preceding triggering pulse.
2. A spark source according to claim 1,
in which said variable timing means includes a zero crossing detector, and means for supplying alternating current power to said high voltage transformer and said zero crossing detector.

3. A spark source according to claim 2, in which said variable timing means includes a phase angle detector, and means for supplying alternating current power to said high voltage transformer and said phase angle detector.

4. A method of producing successive sparks for spectroscopic analysis,
by discharging a capacitor across a spark gap,
recharging the capacitor from a rectified alternating voltage source,
and repeating the discharging and charging operations,
while timing the discharging of the capacitor in each instance to occur when the capacitor has been recharged to a particular voltage,
the timing of the discharging of the capacitor being done in relation to the phase angle of the rectified alternating voltage source.

5. A spark source, comprising
a high voltage transformer having a secondary winding for supplying alternating current at a high voltage,
a storage capacitor,
a charging circuit including a rectifier connected between said secondary winding and said capacitor for charging said capacitor,
spark gap electrodes having a spark gap therebetween,
a discharge circuit including an electronic switching device connected between said capacitor and said spark gap electrodes for discharging said capacitor across said spark gap,
said electronic switching device having input means for receiving triggering signals,
and control means for supplying a sequence of variably spaced triggering pulses to said input means for producing a sequence of spark cycles in which said capacitor is charged to substantially equal voltages for all of said spark cycles,
said control means including variable timing means for producing each triggering pulse at a time when said capacitor has been charged to a particular voltage.

6. A spark source according to claim 5,
in which said variable timing means includes phase detector means,
means for supplying said transformer and said phase detector means with alternating current power,
and means responsive to said phase detector means for deriving the timing of each triggering pulse.

7. A spark source according to claim 6,
in which said phase detector means includes a zero crossing detector.

8. A method of producing successive sparks for spectroscopic analysis,
by discharging a capacitor across a spark gap,
recharging the capacitor from a rectified alternating voltage source,
and repeating the discharging and charging operations,
while timing the discharging of the capacitor in each instance to occur when the capacitor has been recharged to a particular voltage,
the timing of the discharging of the capacitor being done in relation to the phase angle of the rectified alternating voltage source by computing the timing from said phase angle and the elapsed time subsequent to the previous discharging of the capacitor.

9. A spark source,
comprising a storage capacitor,
charging means for charging said capacitor,
spark gap electrodes having a spark gap therebetween,
a discharge circuit including inductance means and an electronic switching device connected in series with said capacitor and said spark gap,
said electronic switching device being operable between a nonconductive state and a unidirectionally conductive state to discharge said capacitor through said inductance means and across said spark gap,
a shunting diode connected in parallel with said electronic switching device and polarized to be unidirectionally conductive in a direction opposite to the conductive direction of said electronic switching device,
said capacitor and said inductance means producing an oscillatory discharge current which is conducted in one direction by said electronic switching device and in the opposite direction by said shunting diode,
and second inductance means in series with said electronic switching device for improving the commutation between said electronic switching device and said shunting diode.

10. A spark source according to claim 9,
in which said electronic switching device comprises a thyratron.

11. A spark source according to claim 9,
in which said electronic switching device comprises a gaseous switching tube.

12. A spark source according to claim 9,
including third inductance means in series with said shunting diode for producing additional improvement in the commutation between said electronic switching device and said shunting diode.

13. A spark source according to claim 9,
in which said second inductance means has sufficient inductance to maintain said electronic switching device in a conductive state during the half-cycles when said shunting diode is carrying the capacitor discharge current.

14. A spark source according to claim 13,
in which said third inductance means has sufficient inductance to maintain conduction in said shunting diode during the half-cycles when said electronic switching device is carrying the capacitor discharge current.

15. A spark source,
comprising a high voltage transformer having a primary winding and a high voltage secondary winding,
means for supplying alternating current to said primary winding,
a storage capacitor,
a charging circuit including a rectifier connected between said secondary winding and said capacitor for supplying high voltage rectified pulses to said capacitor for charging said capacitor,
spark gap electrodes having a spark gap therebetween,
a discharge circuit including an electronic switching device connected between said capacitor and said spark gap electrodes for discharging said capacitor across said spark gap, said electronic switching device having input means for receiving triggering signals, and control means for supplying a sequence of triggering pulses to said input means for producing a sequence of spark cycles in which said capacitor is charged by said charging circuit and then is discharged through said electronic switching device and across said spark gap, said control means including variable timing means for varying the timing of each of said triggering pulses with respect to the phase angle of the alternating current to vary the voltage to which said capacitor is charged for each spark discharge.

16. A spark source according to claim 15, in which said control means includes means for producing one of said triggering pulses corresponding to each of said high voltage pulses supplied by said charging circuit to said capacitor, said timing means being operative to vary the timing of each of said triggering pulses with respect to the phase angle of said alternating current.

17. A spark source according to claim 16, in which said control means includes pulse generating means for producing said triggering pulses, said timing means including variable phase shifting means, means for supplying said alternating current to said variable phase shifting means, and phase detecting means connected between said phase shifting means and said pulse generating means for varying the timing of said triggering pulses in response to the shifting of the phase by said variable phase shifting means.

18. A spark source according to claim 15, in which said control means includes pulse generating means for producing a plurality of said triggering pulses corresponding to each of said high voltage pulses supplied to said capacitor by said charging circuit, said timing means including means for varying the timing of each of said plurality of pulses with respect to the phase angle of said alternating current.

19. A spark source according to claim 15, in which said control means includes pulse generating means for producing a plurality of said triggering pulses corresponding to each of said high voltage rectified pulses supplied by said charging circuit to said capacitor, said timing means including a plurality of variable means for individually varying the timing of said plurality of triggering pulses with respect to the phase angle of said alternating current.

20. A spark source according to claim 15, in which said control means includes pulse generating means for producing a plurality of said triggering pulses corresponding to each of said high voltage rectified pulses supplied by said charging circuit to said capacitor, said timing means including a phase angle detector, means for supplying said alternating current to said phase angle detector, said phase angle detector including means for producing phase locking pulses corresponding to the phase angle of said alternating current, and variable means connected between said phase angle detector and said pulse generating means for individually varying the timing of each of said plurality of triggering pulses with respect to the timing of said phase locking pulses.

21. A spark source according to claim 15, in which said control means includes pulse generating means for producing a plurality of said triggering pulses corresponding to each of said high voltage rectified pulses supplied by said charging circuit to said capacitor, said timing means including a phase angle detector, means for supplying said alternating current to said phase angle detector, said phase angle detector including means for producing phase locking pulses corresponding to the phase angle of said alternating current, and a plurality of individually variable delay elements connected between said phase angle detector and said pulse generating means for individually varying the delay between the phase locking pulses and each of said plurality of triggering pulses.

22. A spark source according to claim 21, in which each of said delay elements comprises a variable monostable multivibrator.

* * * * *

UNITED STATES PATENT OFFICE
CERTIFICATE OF CORRECTION

Patent No. 4,055,783  Dated October 25, 1977

Inventor(s) John P. Walters and David M. Coleman

It is certified that error appears in the above-identified patent and that said Letters Patent are hereby corrected as shown below:

In Column 12, line 34, "of" should be --or--

In Column 17, line 14, "where" should be --which--

In Column 18, line 12, "blow" should be --below--

In Column 18, line 26, "ration" should be --ratio--

In Column 18, line 62, insert --186-- after "lead"

In Column 22, lines 29 and 30, after "circuit 320" delete "and a pulse duration circuit 322. The timing or delay circuit" .

Signed and Sealed this

Twenty-seventh Day of June 1978

[SEAL]

Attest:

RUTH C. MASON
Attesting Officer

DONALD W. BANNER
Commissioner of Patents and Trademarks